(12) United States Patent
Lenhert et al.

(10) Patent No.: US 9,447,446 B2
(45) Date of Patent: Sep. 20, 2016

(54) LIPID MULTILAYER MICROARRAYS AND THEIR USE FOR CELL CULTURE SCREENING

(75) Inventors: Steven Lenhert, Tallahassee, FL (US); Aubrey Kusi-Appiah, Tallahassee, FL (US)

(73) Assignee: FLORIDA STATES UNIVERSITY RESEARCH FOUNDATION, Tallahassee, FL (US)

(*) Notice: Subject to any disclaimer, the term of this patent is extended or adjusted under 35 U.S.C. 154(b) by 240 days.

(21) Appl. No.: 13/534,772

(22) Filed: Jun. 27, 2012

(65) Prior Publication Data
US 2013/0137599 A1 May 30, 2013

Related U.S. Application Data

(60) Provisional application No. 61/501,298, filed on Jun. 27, 2011, provisional application No. 61/577,834, filed on Dec. 20, 2011.

(51) Int. Cl.
*C12Q 1/25* (2006.01)
*B01L 3/00* (2006.01)
*C12Q 1/00* (2006.01)
*C12Q 1/02* (2006.01)
*G01N 33/50* (2006.01)
*G01N 33/543* (2006.01)

(52) U.S. Cl.
CPC ............ *C12Q 1/025* (2013.01); *G01N 33/5008* (2013.01); *G01N 33/5432* (2013.01); *B01L 3/5088* (2013.01)

(58) Field of Classification Search
CPC ............................ C12Q 1/025; G01N 33/5432
USPC ............................................................ 435/4
See application file for complete search history.

(56) References Cited

U.S. PATENT DOCUMENTS

2006/0094053 A1* 5/2006 Stamou et al. ............... 435/6
2012/0258292 A1 10/2012 Lenhert

OTHER PUBLICATIONS

Pompeo et al., 2005, Biochimica et Biophysica Acta—Biomembranes, 1712, 29-36.*
Yamazaki et al., 2005, BMC Biotechnology, 5, 18, pp. 1-11.*
Bailey, S.N., et al., "Microarrays of small molecules embedded in biodegradable polymers for use in mammalian cell-based screens," Proc. Natl. Acad. Sci., vol. 101, No. 46, Nov. 2004, pp. 16144-16149.
Braunschweig, A.B., et al. "Molecular Printing," Nature Chemistry, vol. 1, Aug. 2009, pp. 353-358.
Chen, D.S., et al. "Molecular and functional analysis using live cell microarrays," Current Opinion in Chemical Biology, vol. 10, 2006, pp. 28-34.
DeLigio, J.T., et al. "Can the status of the Breast and Ovarian Cancer Susceptibility Gene 1 product (BRCA1) predict response to taxane-based cancer therapy?" Anticancer Agents Med. Chem., vol. 9, No. 5, Jun. 2009, pp. 543-549.

(Continued)

*Primary Examiner* — Sharmila G. Landau
*Assistant Examiner* — Sheridan Macauley
(74) *Attorney, Agent, or Firm* — Fox Rothschild LLP

(57) ABSTRACT

Provided is a device having one or more lipid multilayer arrays of lipid multilayer structures on a substrate. Each lipid multilayer structure encapsulates an encapsulated material that may be delivered to a cell that is in contact with the lipid multilayer structure to determine the cellular response of the cell to the encapsulated material.

22 Claims, 22 Drawing Sheets

(56) References Cited

OTHER PUBLICATIONS

DiMasi, J.A., et al., "The price of innovation: new estimates of drug development costs," Journ. of Health Economics, vol. 22, 2003, pp. 151-185.
Dittrich, P.S., et al., "Lab-on-a-chip: microfluidics in drug discovery," Nature, vol. 5, Mar. 2006, pp. 210-218.
Dove, A., "High-throughput screening goes to school," Nature Methods, vol. 4. No. 6, Jun. 2007, pp. 523-532.
Ginger, D.S., "The Evolution of Dip-Pen Nanolithography," Angew. Chem. Int. Ed. vol. 43, No. 1, Dec. 2003, pp. 30-45.
Gomez-Sjoberg, R., et al., "Versatile, Fully Automated, Microfluidic Cell Culture System," Anal. Chem., vol. 79, 2007, pp. 8557-8563.
Gregoriadis, G., Engineering liposomes for drug delivery: progress and problems, Trends Biotechnol. vol. 13, 1995, pp. 527-537.
Haaheim, J., et al., "Dip Pen Nanolithography: A "Desktop Nanofab" Approach Using High-Throughput Flexible Nanopatterning," Scanning, vol. 30, 2008, pp. 137-150.
Hoever, M., et al., "The evolution of microarrayed compound screening," Drug Discovery Today, vol. 9, No. 8, Apr. 2004, pp. 358-365.
Hook, A.L., et al., "Advanced Substrate Fabrication for Cell Microarrays," Biomacromolecules, vol. 10, 2009, 573-579.
Hung, P.J. et al., "Continuous Perfusion Microfluidic Cell Culture Array for High-Throughput Cell-Based Assays," Biotechnology Bioengineering, vol. 89, No. 1, Jan. 2005, pp. 1-8.
Kang, L., et al., "Microfluidics for Drug Discovery and Development: From Target Selection to Product Lifecycle Management," Drug Discovery Today, vol. 13, 2008, pp. 1-13.
Kenan, D.J., et al., "Peptide-PEG Amphiphiles as Brief Communication Cytophobic Coatings for Mammalian and Bacterial Cells," Chemistry & Biology, vol. 13, Jul. 2006, pp. 695-700.
Khademhosseini, AI., "Microscale technologies for tissue engineering and biology," Proc. Natl. Acad. Sci., vol. 103, No. 8, Feb. 2006, pp. 2480-2487.
Koren, E., et al., "Drug Carriers for Vascular Drug Delivery," IUBMB Life, vol. 63, No. 8, Aug. 2011, pp. 586-595.
Kusi-Appiah, A.E., "Lipid multilayer microarrays for in vitro liposomal drug delivery and screening," Biomaterials, vol. 33, 2012, pp. 4187-4194.
Kwon, C.H., et al., "Drug-eluting microarrays for cell-based screening of chemicalinduced apoptosis," Anal Chem., vol. 83, No. 11, Jun. 2011, pp. 4118-4125.
Lenhert, S., et al., "Massively Parallel Dip-Pen Nanolithography of Heterogeneous Supported Phospholipid Multilayer Patterns," Small, vol. 3, No. 1, 2007, pp. 71-75.
Lenhert, S., et al., "Materials Integration by Dip-Pen Nanolithography," Nanotechnology, vol. 6, 2009, pp. 171-196.
Lenhert, S., et al., "Lipid multilayer gratings," Nature Nanotechnology, Letters, vol. 5, No. 1, Feb. 2010, pp. 1-5.
Lenhert, S., et al., "Lipid Dip-Pen Nanolithography for FUnctional Biomimtec Membrane Systems," Nanotechnology, vol. 1, 2008, pp. 513-516.
Li, B., et al., "Patterning Colloidal Metal Nanoparticles for Controlled Growth of Carbon Nanotubes," Advanced Materials, vol. 20, 2008, pp. 4873-4878.
Li, B., et al., "Nanoscale-Controlled Enzymatic Degradation of Poly(L-lactic acid) Films Using Dip-Pen Nanolithography," Small, vol. 7, No. 2, 2011, pp. 226-229.
Malam, Y., et al., "Liposomes and nanoparticles: nanosized vehicles for drug delivery in cancer," Trends in Pharmacological Sciences, vol. 30, No. 11, 2009, pp. 592-599.

Meyvantsson, I., et al., "Automated Cell Culture in High Density Tubeless Microfluidic Device Arrays," Lab Chip, vol. 8, 2008, pp. 717-724.
Nafday, O.A., et al., "High-throughput optical quality control of lipid multilayers fabricated by dip-pen nanolithography," Nanotechnology, vol. 22, 2011, pp. 1-7.
Nafday, O.A., et al., "Multifunctional Lipid Multilayer Stamping," Small, vol. 8, No. 7, 2012, pp. 1021-1028.
Nicholson, R.L., et al., "Small-Molecule Screening: Advances in Microarraying and Cell-Imaging Technologies," ACS Chem. Biol. vol. 2, 2007, pp. 24-30.
Porter, C.J.H., et al., "Lipids and lipid-based formulations: optimizing the oral delivery of lipophilic drugs," Nature Reviews, Drug Discovery, vol. 6, 2007, pp. 231-248.
Riccardi, C., et al., "Analysis of apoptosis by propidium iodide staining and flow cytometry," Nat. Protoc. vol. 1, No. 3, 2006, 1458-1461.
Saha, S.K., et al., "Characterization of the Dip Pen Nanolithography Process for Nanomanufacturing," Journal of Manufacturing Science and Engineering, vol. 133, Aug. 2011, pp. 041005-1-041005-9.
Salaita, S., et al., Massively Parallel Dip-Pen Nanolithography with 55000-Pen Two Dimensional Arrays, Angew. Chem. Int. Ed., vol. 45, 2006, pp. 7220-7223.
Salaita, S., et al., "Applications of dip-pen nanolithography," Nature Nanotechnology, vol. 2, Mar. 2007, pp. 145-155.
Sekula, S., "Multiplexed Lipid Dip-Pen Nanolithography on Subcellular Scales for the Templating of Functional Proteins and Cell Culture," Small, vol. 4, 2008, pp. 1785-1793.
Shimazawa, M., et al., "Involvement of ER stress in retinal cell death," Molecular Vision, vol. 13, 2007, 578-587.
Starkuviene, V., et al., "Transfected Cell Microarrays: An Efficient Tool for High-Throughput Functional Analysis," Expert Rev. Proteomics, vol. 4, No. 4, 2007, pp. 479-489.
Torchilin, V.P., Micellar Nanocarriers: Pharmaceutical Perspectives, Pharm. Res. vol. 24, 2007, pp. 1-16.
Upadhyaya, S., et al., "Microfluidic devices for cell based high throughput screening," Lab on a Chip, vol. 10, 2010, pp. 341-348.
Wang, Y., et al., "A Self-Correcting Inking Strategy for Cantilever Arrays Addressed by an Inkjet Printer and Used for Dip-Pen Nanolithography," Small 2008, vol. 4, No. 10, pp. 1666-1670.
Wang, H.Y., et al., "A microfluidic cell array with individually addressable culture chambers," Biosensors and Bioelectronics, vol. 24, 2008, pp. 613-617.
Weibel, D.B., et al., "Applications of Microfluidics in Chemical Biology," Current Opinion in Chemical Biology, vol. 10, 2007, pp. 584-591.
Whitesides, G.M., "The origins and the future of microfluidics," Nature, vol. 442, Jul. 2006, pp. 368-373.
Wu, J., et al., "A sandwiched microarray platform for benchtop cell-based high throughput screening," Biomaterials, vol. 32, No. 3, Jan. 2011, pp. 841-848.
Wu, L.Y., et al., "Microfluidic self-assembly of tumor spheroids for anticancer drug discovery," Biomed. Microdevices 10, 2008, pp. 197-202.
Xu, F., et al., "Microengineering methods for cell-based microarrays and high-throughput drug-screening applications," Biofabrication, vol. 3, 2011, pp. 1-13.
Yarmush, M.L., "Living-Cell Microarrays," Annu. Rev. Biomed Eng., vol. 11, 2009, pp. 235-257.
Zhang, H., et al., "High-Throughput Dip-Pen-Nanolithography-Based Fabrication of Si Nanostructures," Small, vol. 3, No. 1, 2007, pp. 81-85.

\* cited by examiner

LIPID MULTILAYER MICROARRAYS AND THEIR USE FOR CELL CULTURE SCREENING

CROSS-REFERENCE TO RELATED APPLICATIONS

This application claims benefit of priority to U.S. Provisional Application No. 61/501,298, entitled "LIPOSOME MICROARRAY SURFACE AND THEIR USE FOR CELL CULTURE SCREENING," filed Jun. 27, 2011, and U.S. Provisional Application No. 61/577,834, entitled "HIGH THROUGHPUT SCREENING METHOD AND APPARATUS," filed Dec. 20, 2011, the entire contents and disclosures of which are incorporated herein by reference in their entirety.

This application makes reference to the above-cited references and the following U.S. patent applications: U.S. Provisional Patent Application No. 61/383,775, entitled "HIGH THROUGHPUT OPTICAL QUALITY CONTROL OF PHOSPHOLIPID MULTILAYER FABRICATION VIA DIP PEN NANOLITHOGRAPHY (DPN)," filed Sep. 17, 2010; U.S. Provisional Patent Application No. 61/387,764, entitled "NOVEL DEVICE FOR DETECTING AND ANALYZING AQUEOUS SAMPLES," filed Sep. 21, 2010; U.S. Provisional Patent Application No. 61/387,550, entitled "LIPID MULTILAYER GRATINGS," filed Sep. 29, 2010; U.S. Provisional Patent Application No. 61/387,556, entitled "LIPID MULTILAYER GRATINGS FOR SEMISYNTHETIC QUORUM SENSORS," filed Sep. 29, 2010; U.S. Provisional Patent Application No. 61/451,619, entitled "IRIDESCENT SURFACES AND APPARATUS FOR REAL TIME MEASUREMENT OF LIQUID AND CELLULAR ADHESION," filed Mar. 11, 2011; U.S. Provisional Patent Application No. 61/451,635, entitled "METHODS AND APPARATUS FOR LIPID MULTILAYER PATTERNING," filed Mar. 11, 2011; U.S. Provisional Patent Application No. 61/501,298, entitled "LIPSOME MICROARRAY SURFACE AND THEIR USE FOR CELL CULTURE SCREENING," filed Jun. 27, 2011; U.S. patent application Ser. No. 13/234,540, entitled "OPTICAL METHOD FOR MEASURING HEIGHT OF FLUORESCENT PHOSPHOLIPID FEATURES FABRICATED VIA DIP-PEN NANOLITHOGRAPHY," filed Sep. 11, 2011; U.S. patent application Ser. No. 13/238,498, entitled "INTEGRATED DEVICE FOR ANALYZING AQUEOUS SAMPLES USING LIPID MULTILAYER," filed Sep. 21, 2011; U.S. patent application Ser. No. 13/248,250, entitled "SEMI-SYNTHETIC QUORUM SENSORS," filed Sep. 29, 2011; and U.S. Provisional Patent Application No. 60/570,490, entitled "LIPID MULTILAYER MICROARRAYS FOR IN VITRO LIPOSOMAL DRUG DELIVERY AND SCREENING," filed Dec. 14, 2011. The entire disclosure and contents of these patent applications are incorporated herein by reference.

BACKGROUND

1. Field of the Invention

The present invention relates to lipid multilayer microarrays.

2. Related Art

Bound arrays of small molecules are useful for biochemical screens but are not typically used for cell culture screens because the dosage that cells can receive is limited, and drug candidates with targets inside the cells are missed.

SUMMARY

According to a first broad aspect, the present invention provides a device comprising: a substrate, one or more lipid multilayer arrays on the substrate, wherein each lipid multilayer array of the one or more lipid multilayer arrays comprises one or more lipid multilayer structures, wherein each lipid multilayer structure of each of the one or more lipid multilayer arrays encapsulates an encapsulated material, and wherein each of the one or more lipid multilayer structures is a microstructure.

According to a second broad aspect, the present invention provides a method comprising the following step: (a) delivering one or more encapsulated materials to one or more cells from one or more lipid multilayer structures that are in contact with the one or more cells, wherein each of the one or more encapsulated materials is encapsulated in a respective lipid multilayer structure of the one or more lipid multilayer structures, and wherein each of the one or more lipid multilayer structures is a microstructure.

According to a third broad aspect, the present invention provides a method comprising the following step: (a) determining one or more cellular responses of one or more cells to each encapsulated material of one or more encapsulated materials delivered to the one or more cells from one or more lipid multilayer structures that are in contact with the one or more cells, wherein each of the one or more encapsulated materials is encapsulated in a respective lipid multilayer structure of the one or more lipid multilayer structures, and wherein each of the one or more lipid multilayer structures is a microstructure.

BRIEF DESCRIPTION OF THE DRAWINGS

The accompanying drawings, which are incorporated herein and constitute part of this specification, illustrate exemplary embodiments of the invention and, together with the general description given above and the detailed description given below, serve to explain the features of the invention.

DETAILED DESCRIPTION OF THE PREFERRED EMBODIMENTS

Definitions

Figure 1:
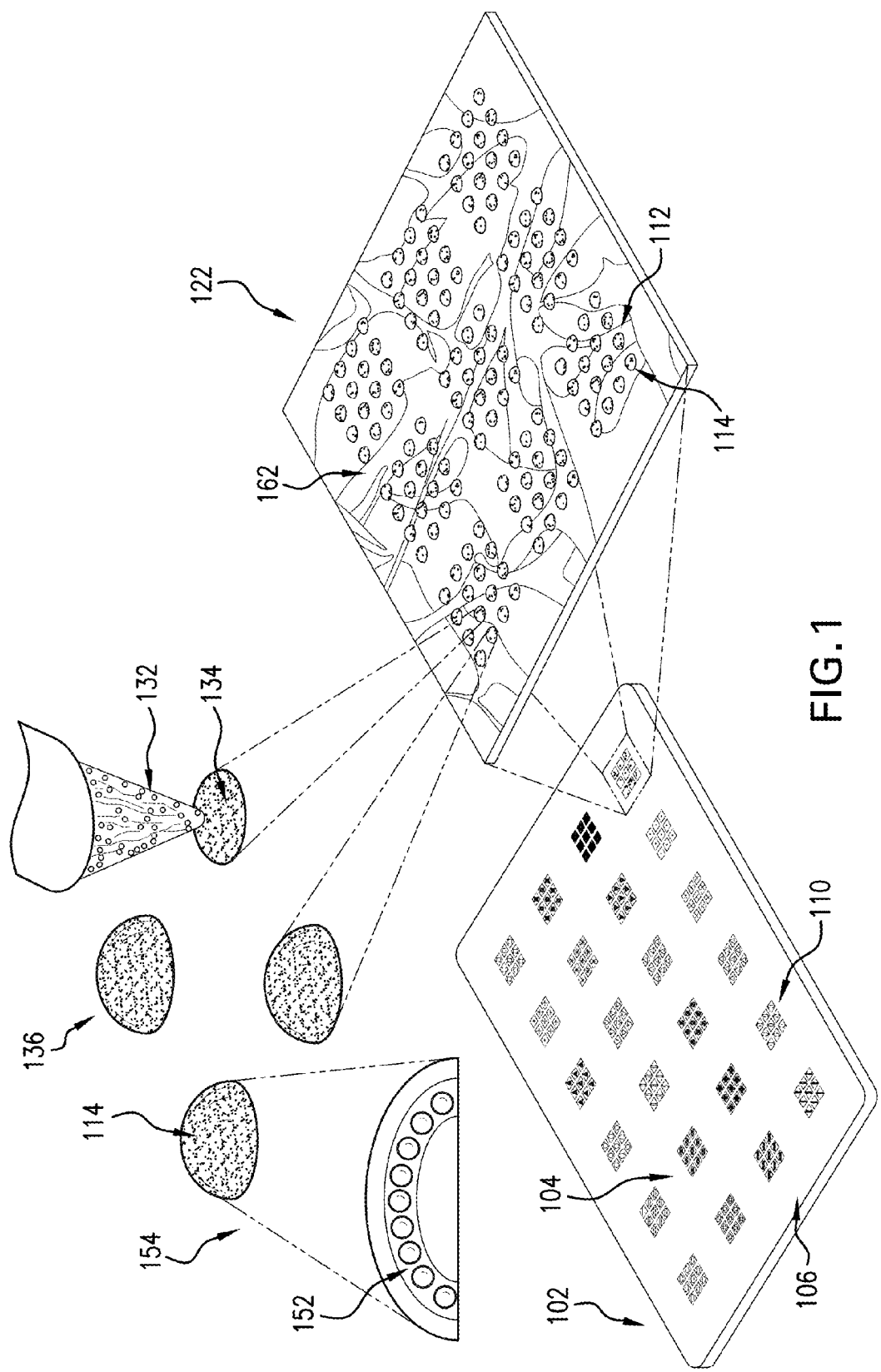
FIG. 1 is schematic illustration of a lipid multilayer microarray chip according to one embodiment of the present invention, a method of making the lipid multilayer chip and zoom views of portions of the lipid multilayer chip.

Where the definition of a term departs from the commonly used meaning of the term, applicant intends to utilize the definitions provided below, unless specifically indicated.

For purposes of the present invention, it should be noted that the singular forms, "a," "an" and "the" include reference to the plural, unless the context as herein presented clearly indicates otherwise.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, a value or property is "based" on a particular value, property, satisfaction of a condition, or other factor, if that value is derived by performing a mathematical calculation or logical decision using that value, property or other factor.

For purposes of the present invention, the term "analyte" refers to the conventional meaning of the term "analyte," i.e., a substance or chemical constituent of a sample that is being detected or measured in a sample.

For purposes of the present invention, the term "array" refers to a one-dimensional or two-dimensional set of microstructures. An array may have any shape. For example, an array may be a series of microstructures arranged in a line, such as an array of squares. An array may be arranged in a square or rectangular grid. There may be sections of the array that are separated from other sections of the array by spaces. An array may have other shapes. For example, an array may be a series of microstructures arranged in a series of concentric circles, in a series of concentric squares, in a series of concentric triangles, in a series of curves, etc. The spacing between sections of an array or between microstructures in any array may be regular or may be different between particular sections or between particular pairs of microstructures. The microstructure arrays of the present invention may be comprised of microstructures having zero-dimensional, one-dimensional or two-dimensional shapes. The microstructures having two-dimensional shapes may have shapes such as squares, rectangles, circles, parallelograms, pentagons, hexagons, irregular shapes, etc.

For purposes of the present invention, the term "biomolecule" refers to the conventional meaning of the term "biomolecule," i.e., a molecule produced by or found in living cells, e.g., a protein, a carbohydrate, a lipid, a phospholipid, a nucleic acid, etc.

For purposes of the present invention, the term "brush" refers to a stamp-like object that is used to create lipid multilayers on the surface by being moved while in contact with the surface.

For purposes of the present invention, the term "camera" refers to any type of camera or other device that senses light intensity. Examples of cameras include digital cameras, scanners, charged-coupled devices, CMOS sensors, photomultiplier tubes, analog cameras such as film cameras, etc. A camera may include additional lenses and filters such as the lenses of a microscope apparatus that may be adjusted when the camera is calibrated. A camera may be used in performing an assay of the present invention. A camera may be used to detect the fluorescent intensities of cells, a lipid multilayer spot of an array, a lipid multilayer dot of an array, etc.

For purposes of the present invention, the term "dehydrated lipid multilayer grating" refers to a lipid multilayer grating that is sufficiently low in water content that it is no longer in fluid phase.

For purposes of the present invention, the term "deliver" refers to the transfer of an encapsulated material, such as a drug, from a lipid multilayer structure to a cell in contact with the structure. An encapsulated material may be "delivered" by various means. In one embodiment of the present invention, an encapsulated material is delivered to a cell by the cell taking up a dot (lipid multilayer microstructure) that encapsulates the encapsulated material. The dot is part of an array on a substrate and the cell takes up the dot by direct contact with the dot and fusion of the dot with the cell membrane by endocytosis.

For purposes of the present invention, the term "detector" refers to any type of device that detects or measures light. A camera is a type of detector.

For purposes of the present invention, the term "dot" refers to an individual lipid multilayer microstructure of an array.

For purposes of the present invention, the term "drug" refers to any chemical substance that affects the functioning of a cell. A drug may be natural or synthetic. Although only particular drugs are described as being used in the examples below, almost any type of drug may be used in the embodiments of the present invention. For example, a drug may be a biomolecule. A drug may be tagged with a marker, such as a fluorescent marker, a radioactive marker, etc. to allow the drug to be tracked in an assay.

For purposes of the present invention, the term "drug pattern" refers to a lipid multilayer array including lipid multilayer microstructures encapsulating a particular drug. For example, a DOTAP pattern is a lipid multilayer array in which the lipid multilayer structures of the array encapsulate DOTAP, a valinomycin pattern is a lipid multilayer array in which the lipid multilayer structures of the array encapsulate valinomycin, a docetaxel pattern is a lipid multilayer array in which the lipid multilayer structures of the array encapsulate docetaxel, etc.

For purposes of the present invention, the term "encapsulate" refers to a material, such as a drug, that is contained in, confined by or otherwise held by a lipid multilayer structure. A portion of an encapsulated material may protrude from a lipid multilayer structure and still be encapsulated by structure.

For purposes of the present invention, the term "encapsulated material" refers to any material that is encapsulated in a lipid multilayer structure. Examples of encapsulated materials include drugs; small molecules, such as drug candidates; lipid additives, such as functionalized phospholipids or cholesterol; larger molecules, such as nucleic acids including DNA, RNA, etc., different from peptides, proteins, etc.; microparticles, nanoparticles. An encapsulated material may be tagged with a marker, such as a fluorescent marker, a radioactive marker, etc. to allow the encapsulated material to be tracked in an assay.

For purposes of the present invention, the term "fluorescence" refers to the conventional meaning of the term "fluorescence," i.e., the emission of light by a substance that has absorbed light or other electromagnetic radiation of a different wavelength.

For purposes of the present invention, the term "fluorescent" refers to any material or mixture of materials that exhibits fluorescence.

For purposes of the present invention, the term "fluorescent dye" refers to any substance or additive that is fluorescent or imparts fluorescence to another material. A fluorescent dye may be organic, inorganic, etc.

For purposes of the present invention, the term "fluorescent microstructure" refers to a microstructure that is fluorescent. A fluorescent microstructure may be made of a naturally fluorescent material or a fluorescent microstructure may be made of a nonfluorescent material, such as a phospholipid, that is doped with a fluorescent dye.

For purposes of the present invention, the term "fluorescent nanostructure" refers to a nanostructure that is fluorescent. A fluorescent nanostructure may be made of a naturally fluorescent material or may be made of a nonfluorescent material, such as a phospholipid, doped with a fluorescent dye.

For purposes of the present invention, the term "fluid" refers to a liquid or a gas.

For purposes of the present invention, the term "freezing by dehydration" refers to removal of residual water content, for instance by incubation in an atmosphere with low water content, for instance a vacuum (<50 mbar) or at relative humidity below 40% (at standard temperature and pressure).

For purposes of the present invention, the term "grating" refers to an array of dots, lines, or 2D shapes that are regularly spaced at a distance that causes coherent scattering of incident light.

For purposes of the present invention, the term "hardware and/or software" refers to digital software or digital hardware, or a combination of both digital hardware and digital software.

For purposes of the present invention, the term "light," unless specified otherwise, refers to any type of electromagnetic radiation. Although, in the embodiments described below, the light that is incident on the gratings or sensors is visible light, the light that is incident on the gratings or sensors of the present invention may be any type of electromagnetic radiation, including infrared light, ultraviolet light, etc., that may be scattered by a grating or sensor. Although, in the embodiments described below, the light that is scattered from the gratings or sensors and detected by a detector is visible light, the light that is scattered by a grating or sensor of the present invention and detected by a detector of the present invention may be any type of electromagnetic radiation, including infrared light, ultraviolet light, etc., that may be scattered by a grating or sensor.

For purposes of the present invention, the term "light source" refers to a source of incident light that is scattered by a grating or sensor of the present invention. In one embodiment of the present invention, a light source may be part of a device of the present invention. In one embodiment of the present invention, a light source may be light that is present in the environment of a sensor or grating of the present invention. For example, in one embodiment of the present invention a light source may be part of a device that is separate from the device that includes the sensors and detector of the present invention. A light source may even be the ambient light of a room in which a grating or sensor of the present invention is located. Examples of a light source include a laser, a light-emitting diode (LED), an incandescent light bulb, a compact fluorescent light bulb, a fluorescent light bulb, etc.

For purposes of the present invention, the term "line" refers to "line" as this term is commonly used in the field of nanolithography to refer to a one-dimensional shape.

For purposes of the present invention, the term "lipid" refers to the conventional meaning of the term "lipid." Lipids include fats, waxes, sterols, fat-soluble vitamins (such as vitamins A, D, E, and K), monoglycerides, diglycerides, triglycerides, phospholipids, etc.

For purposes of the present invention, the term "lipid ink" refers to any material comprising a lipid used in printing a lipid structure on a substrate.

For purposes of the present invention, the term "lipid multilayer" refers to a lipid coating that is thicker than a single bilayer (>5 nm).

For purposes of the present invention, the term "lipid multilayer array" refers to an array comprising lipid multilayer structures.

For purposes of the present invention, the term "lipid multilayer microarray" refers to a lipid multilayer array in which the lipid multilayer structures are microstructures and/or nanostructures.

For purposes of the present invention, the term "lipid multilayer grating" refers to a grating comprising lipid multilayers.

For purposes of the present invention, the term "lipid multilayer structure" refers to a structure comprising one or more lipid multilayers. A lipid multilayer structure may include a dye such as a fluorescent dye.

For purposes of the present invention, the term "lipid structure" refers to a structure comprising a lipid.

For purposes of the present invention, the term "liposome" refers to the a vesicle composed of a lipid bilayer or a lipid multilayer, such as a lipid multilayer structure.

For purposes of the present invention, the term "low humidity atmosphere" refers to an atmosphere having a relative humidity of less than 40%.

For purposes of the present invention, the term "lyotropic" refers to the conventional meaning of the term "lyotropic," i.e., a material that forms liquid crystal phases because of the addition of a solvent.

For purposes of the present invention, the term "microarrayer" refers to a device used to form a microarray. For example, a microarrayer may be a pin-spotter, inkjet printer, dip-pen nanolithography tip, etc.

For purposes of the present invention, the term "microstructure" refers to a structure having at least one dimension smaller than 1 mm. A nanostructure is one type of microstructure.

For purposes of the present invention, the term "nanostructure" refers to a structure having at least one dimension on the nanoscale, i.e., a dimension between 0.1 and 100 nm.

For purposes of the present invention, the term "neat lipid ink" refers to a lipid ink consisting of a single pure lipid ink.

For purposes of the present invention, the term "palette" refers to a substrate having one or more lipid inks that are made available to be picked up or drawn into the recesses or other topographical or chemical features of a stamp. The one or more lipid inks may be located in recesses, inkwells, etc., in the palette, or deposited onto a flat palette.

For purposes of the present invention, the term "patterned array" refers to an array arranged in a pattern. A patterned array may comprise a single patterned array of lipid multilayer structures or two or more patterned arrays of lipid multilayer structures. Examples of patterned arrays of lipid multilayer structures include a patterned array of dots, a patterned array of lines, a patterned array of squares, etc.

For purposes of the present invention, the term "plurality" refers to two or more. Therefore, an array of microstructures having a "plurality of heights" is an array of microstructures having two or more heights. However, some of the fluorescent microstructures in an array having a plurality of heights may have the same height.

For purposes of the present invention, the term "recess" refers to a recess of any size or shape in a stamp or brush. A recess may have any cross-sectional shape such as a line, a rectangle, a square, a circle, an oval, etc. The dimensions of a recess may change depending on the depth of the recess. For example, a recess may be wider at the top of the recess than at the bottom of the recess, such as in a V-shaped recess.

For purposes of the present invention, the term "recess pattern" refers to the pattern made by one or more recesses of a stamp or brush.

For purposes of the present invention, the term "regular pattern" refers to a pattern of ridges and recesses organized in a specific geometric pattern. For example, a series of parallel recesses and/or lines is one example of a regular pattern. One or more arrays of ridges and recesses arranged in a square, a circle, an oval, a star, etc., is another example of a regular pattern.

For purposes of the present invention, the term "ridge" refers to any raised structure. A ridge is not limited to a linear ridge, unless clearly specified otherwise in the description below. A ridge may have any cross-sectional shape such as a line, a rectangle, a square, a circle, an oval, etc. The dimensions of a ridge may change depending on the depth of a neighboring groove. For example, a ridge may be wider at the bottom of the ridge than at the top of the ridge, such as in a V-shaped ridge. A ridge may constitute the entire contacting surface of a stamp or brush after recesses have been formed, etched, etc., into the stamp or brush.

For purposes of the present invention, the term "scattering" and the term "light scattering" refer to the scattering of light by deflection of one or more light rays from a straight path due to the interaction of light with a grating or sensor. One type of interaction of light with a grating or sensor that results in scattering is diffraction.

For purposes of the present invention, the tam "sensor" and the term "sensor element" are used interchangeably, unless specified otherwise, and both terms refer to a material that may be used to sense the presence of an analyte.

For purposes of the present invention, the term "spot" refers to an area of a defined area of a surface coated with a material that was at some point in the manufacturing process produced from a single delivery event from a microarrayer. In the context of lipid multilayer structures formed by stamping, a "spot" is an area of a final patterned surface that originates from a single spot on the ink palette.

For purposes of the present invention, the term "square" refers to a microstructure that is square in shape, i.e., it has a two-dimensional shape wherein all sides are equal.

For purposes of the present invention, the term "stamp" refers to an object that has recesses for holding lipid ink and that is used to create lipid multilayers on a surface of a substrate. Lipid multilayer structures may be formed by a stamp having lipid ink thereon contacting the substrate or the substrate contacting the stamp that has lipid ink thereon so that the lipid ink is pulled from the stamp and deposited on the substrate.

For purposes of the present invention, the term "topographically structured brush" refers to a brush having recesses that form one or more recess patterns.

For purposes of the present invention, the term "topographically structured stamp" refers to a stamp having recesses that form one or more recess patterns.

Description

Screening for effects of small molecules on cells grown in culture is a well-established method for drug discovery and testing, and faster throughput at lower cost is needed. Small-molecule arrays and microfluidics are promising approaches. In one embodiment, the present invention provides surface-mediated delivery of drugs to cells from a microarray of phospholipid multilayers (layers thicker than a bilayer) encapsulating small molecules. The multilayer patterns are of sub-cellular dimensions and controllable thickness and are formed by dip-pen nanolithography. The patterns successfully delivered a rhodamine-tagged lipid and drugs only to the cells directly over them, indicating successful encapsulation and no cross-contamination to cells grown next to the patterns. In one embodiment, the present invention provides the multilayer thickness-dependent uptake of lipids from dots with sub-cellular lateral dimensions, and therefore provides the delivery of different dosages from different areas of the array. The efficacies of two drugs are assayed on the same surface, and it is possible to deliver dosages comparable to those of solution-based delivery (up to the equivalent of 30 µg/mL). These results indicated that it is possible to produce a single high-throughput liposome-based screening microarray plate that can be used in the same way as a standard well plate.

In the pharmaceutical industry, high-throughput screening (HTS) for the effects of compounds on cells grown in culture is an essential first step in identifying potential drugs for further development.[1] Currently, the method used involves microtiter plate technology that uses microwells (e.g., 1536 wells per plate).[1] Hundreds of thousands of compounds can be screened by HTS, but current methods require large amounts of materials (cells, compounds, reagents) and time, especially to grow the cells, and cost from $50 million to $2 billion every year in the United States or approximately $100,000 worth of consumables and two months per screen.[2] Attention has, therefore, shifted toward advancements in miniaturization of the screening methodology, which could reduce the cost and increase the throughput of drug screening.[3]

Two promising approaches to miniaturization of HTS are those of microfluidics and microarrays.[4] The former approach (also known as lab-on-a-chip) advances by using smaller and smaller wells and small fluidic circuitry to deliver the different reagents to the miniaturized wells.[5,6,7] Pneumatic valves, for example, have been used to control delivery into microfluidic chambers, so that different cell types with the same treatment or one cell type with different treatments can be directed to designated culture chambers for observation and analysis.[8] In addition, versatile, fully automated microfluidic cell culture systems have been designed to create independent and arbitrary media formulations in 96-well systems, allowing for manipulation and customization of culture conditions.[9] The surface tension created by the unequal droplet volumes on structured surfaces drives flow in passive structures and makes automated cell culture in high-density tubeless microfluidic-device arrays possible. The method can therefore be integrated with existing laboratory infrastructure without the use of discrete microcomponents for monolayer and 3D cell culture systems.[10] Moreover, microfluidic hydrodynamic trapping of cells has been used to create spheroids with constant perfusion of media in controlled geometry for potential use in anticancer drug arrays.[11] These and other microfluidic approaches represent a substantial advancement in high-throughput, automated materials delivery to cells at lower reagent volumes and cost, but because microfluidics is an emerging technology that typically involves a significant change from the more-established microwell format used in HTS labs for cell culture, issues of scalability, device optimization and long-term cell viability must still be considered.[12] The small-molecule microarray approach uses a different strategy in which the compounds to be screened are arrayed onto a surface. Cells are then cultured on or near that surface, and the cellular response to each drug is assayed at each position on the microarray.[4,13,14,15,16,17]

Although covalently bound arrays of small molecules are useful for biochemical screens, they are not typically used for cell culture screens because the dosage that cells can receive is limited, and drug candidates with targets inside the cells are missed. A reliable assay requires that the drug compounds be delivered to the cells in sufficiently high dosages. One approach uses techniques that involve patterning on surfaces of cell-adhesive materials such as poly-$_L$-lysine that have been loaded with materials to be screened.[18] Cells cultured on these surfaces bind only to the patterned spots, so different molecules can be screened simultaneously.[4,18] Small-molecule microarrays of biopolymer-impregnated spots have been used to deliver drugs to cells in a dose-dependent manner, thereby allowing for screening of small molecules for efficacy and dose-response. Small molecules diffusing out of these spots affect the cells locally,[19] but this approach is suitable only for water-soluble drugs because the small molecules must diffuse out of these spots to exert their effects,[19] and cross-contamination between neighboring spots can occur. Cell microarray systems have also been fabricated that use surface patterning and microfluidic methods for loading drugs.[20,21]

These spots can then be used as arrays to analyze or screen different drugs. Another approach is the sandwiched microarray method, which avoids the cross-contamination problem by using cell-filled microwells into which drug-spotted polydimethylsiloxane micropillars are inserted.[22] A general challenge in the microarray format is to deliver enough of the drug to the cells to obtain reliable efficacy data without cross-contamination and ideally without increasing the complexity of the experimental procedure.

The use of lipids as vectors for delivery of materials to cells has become a widely studied field because of its potential for delivery of both lipophilic and hydrophilic drugs and nutrients through liposomes.[23,24] The efficiency of delivery from solution by means of various phospholipids has been quite extensively studied, and the efficient delivery into various cells using phospholipids has made them the preferred material for use in screenings.[25,26,27,28] Dip-pen nanolithography (DPN) is a method of surface patterning that uses the tip of the probe of an atomic force microscope to print materials onto surfaces. This method has been used recently to deposit various materials, including proteins and phospholipids, onto the surfaces of materials such as glass, polystyrene and silicon chips with lateral resolution down to 100 nm.[29,30,31,32] The self-organization properties of phospholipids enable them to stack controllably into multilayer structures.[29] Importantly, DPN allows for the fabrication of lipid multilayer nanostructures on surfaces at controllable thicknesses and for the encapsulation within them of other materials. Furthermore, arrays of 55,000 tips per square centimeter have been used, and the ability of different tips in a parallel array to print different phospholipid mixtures onto the same surface has been demonstrated. These methods can be combined for production of massively parallel and multiplexed material patterns.[33]

In one embodiment, the present invention provides a combination of scalable pin-spotting microarray technology with the process of lipid multilayer stamping in order to generate nanostructured lipid multilayer microarrays suitable for cell culture applications such as screening of liposomal drug formulations on a chip.

In one embodiment of the present invention, a process is provided for microarraying lipid multilayers to create spots on a substrate, such as a flat or structured polydimethylsiloxane (PDMS) substrate or "ink-palette" and subsequently transferring these spots into dots by means of multilayer stamping to produce lipid multilayer structures. In one embodiment, the present invention provides a combination of scalable pin-spotting microarray technology with a process of lipid multilayer stamping in order to generate nanostructured lipid multilayer microarrays capable of screening liposomal formulations of encapsulated materials in the dots formed by stamping. In order to improve spot uniformity an ink palette may be used to ink the structured stamp. That is, the inks would be arrayed onto a flat or structured surface, then the structured or flat stamp would be placed in contact with the ink-palette, and finally used for lipid multilayer stamping. Stamping may be used to create spots composed of lipid nanostructures. In the context of lipid multilayer structures formed by stamping, a "spot" is an area of a final patterned surface that originates from a single spot on the ink palette. The finer structures that make up the spot in the resulting array are dots, microstructures or nanostructures. In one embodiment of the present invention, the thickness of these structures is on the order of 10-100 nanometers, with the lateral dimensions typically being several micrometers. In other embodiments the thicknesses are greater than 100 nanometers. In lipid multilayer stamping, lipids are arrayed onto a structured elastomeric stamp, which is then used to create lipid multilayer patterns. Lipid multilayer stamping techniques that may be used in various embodiments of the present invention are described in U.S. patent application Ser. No. 13/417,588 to Lenhert et al., entitled "Method and apparatus for lipid multilayer patterning," filed Mar. 12, 2012, and in O. A. Nafday, T. W. Lowry, S. Lenhert, "Multifunctional lipid multilayer stamping," *Small* 8(7), 1021-28 (2012), the entire contents and disclosures of which are incorporated herein by reference.

In one embodiment, the present invention provides a small-molecule microarray based on the use of lipid multilayer structures formed on surfaces by DPN (FIG. 1). Molecules can be encapsulated within multilayer patterns of phospholipids for delivery to cells. Lipids have negligible solubility in water, so their use has the potential to solve the cross-contamination problem in small-molecule microarrays. Furthermore, the ability to control lipid multilayer thickness by means of DPN provides a method of locally controlling the dosage that a cell will receive. To demonstrate the use of lipid multilayer microarrays for delivery to cells, fluorescently labeled lipids and cytotoxic lipophilic drugs are delivered to the cells and are assayed for toxicity.

FIG. 1 is a schematic illustration of a lipid multilayer microarray chip 102 according to one embodiment of the present invention comprising lipid multilayer microarray 104 deposited on a substrate 106. Each square array 110 of lipid multilayer microarray 104 includes nine dot arrays 112 arranged in a 3×3 array. Each dot array 112 includes sixteen dots 114 arranged in a 4×4 array as shown in zoom-in 122. Therefore, each square array 110 includes 144 dots 114 as shown in zoom-in 122. Each dot 114 is deposited by a DPN tip 132 coated with a lipid/drug mixture 134 as shown by zoom-in 136. Each dot 114 encapsulates a drug 152 as shown by zoom-in 154. Dots 114 of each dot array 112 encapsulate a single drug and may encapsulate a particular dose of a single drug. In lipid multilayer microarray 104, different drugs are delivered by different square arrays 110 as indicated by the different "colors" of square arrays 110. Cells 162 are cultured over lipid multilayer microarray chip 102 as shown by zoom-in 122 allowing the drugs encapsulated in dots 114 to be delivered into cells 162 by the process of endocytosis in which dots 114 are taken into cells 162.

A supported lipid multilayer microarray such as that shown in FIG. 1 has advantages over other techniques, such as small molecule microarrays for drug screening.[44] In small molecule microarrays, small molecules (drug candidates in the case of drug screening applications) are covalently attached to a surface, and cells can be grown on the surface. However, the covalent attachment of the small molecule on the surface prevents internalization of the compounds, limiting the types of tests that can be carried out. Furthermore, the number of molecules that a single cell can interact with is limited by the surface area the cell contacts. Diffusion of small molecules from array sources, such as gels, has also been used for screening, although molecular diffusion limits the applicability of those methods.

In contrast, using surface-supported lipid multilayers encapsulating drug candidates instead of covalently binding the molecules to the surface solves these problems. In one embodiment, the present invention provides a method that may be used for screening of delivery systems, and may be particularly important for lipophilic drug candidates.

In one embodiment, the present invention provides a method for drug-resistance cell screening, where cells from biopsies (typically cancer cells) are cultured ex situ. Because of limited numbers of primary cells, efficient assays are required, and the microarray format described here minimizes sample requirements.

The use of lipids as delivery vectors to cells has become a widely studied field due to the potential for utilizing them to deliver both lipophilic and hydrophilic drugs through liposomes. The efficiency of delivery from solution using various phospholipids has been quite extensively studied, making phospholipids a useful material for use in screening for their efficient delivery into various cells.

Dip-pen nanolithography (DPN) is a method of delivery of materials onto surfaces using the probe of an atomic force microscope (AFM). This method has been used to deposit various phospholipids onto the surfaces of various materials, see S. Lenhert et al. *Nat. Nanotechnol.* 5, 275 (2010); A. B. Braunschweig, F. W. Huo and C. A. Mirkin, *Nat. Chem.* 1, 353 (2009); S. Lenhert, H. Fuchs and C. A. Mirkin, *Materials Integration by Dip-pen Nanolithography* (Weinheim: Wiley-VCH) (2009); H. Zhang, N. Amro, S. Disawal, R. Elghanian, R. Shile. and J. Fragala, *Small* 3, 81 (2007); B. Li, C. F. Goh, X. Z. Zhou, G. Lu, H. Tantang, Y. H. Chen, C. Xue, F. Y. C. Boey and H. Zhang, *Adv. Mater.* 20, 4873 (2008); H. Li, Q. Y. He, X. H. Wang, G. Lu, C. Liusman, B. Li, F. Boey, S. S. Venkatraman and H. Zhang, *Small* 7, 226 (2011); K. Salaita, Y. H. Wang and C. A. Mirkin, *Nat. Nanotechnol.* 2, 145 (2007); J. Haaheim and O. N. Nafday, *Scanning* 30, 137 (2008); and D. S. Ginger, H. Zhang and C. A. Mirkin, *Angew. Chem. Int. Ed.* 43, 30 (2004), the entire contents and disclosures of which are incorporated herein by reference. Using phospholipids as the ink for DPN allows control of the lipid multilayer stacking (height) and biocompatible material integration on solid surfaces, see S. Sekula et al., *Small* 4, 1785 (2008); and Y. H. Wang, L. R. Giam, M. Park, S. Lenhert, H. Fuchs and C. A. Mirkin, *Small* 4, 1666 (2008), the entire contents and disclosures of which are incorporated herein by reference.

In addition, DPN allows for multiplexed printing of phospholipids. As these lipids are also used as delivery vehicles for various materials, it seems that one of the most logical next steps to take is to use these arrays to deliver materials into cells.

In one embodiment, the present invention provides a method for delivering lipophilic molecules to cells from lipoplexed patterns of phospholipids mixed with the drugs. To do this, the lipid multilayers encapsulating the drugs would have to remain localized to the printed spots. DPN provides the method of simultaneous deposition of many different formulations on surfaces at low cost. In one embodiment, the present invention provides a method that may increase the range of screening from hundreds to thousands and even millions over the same area as that of a microtiter plate of compounds.

Figure 2:
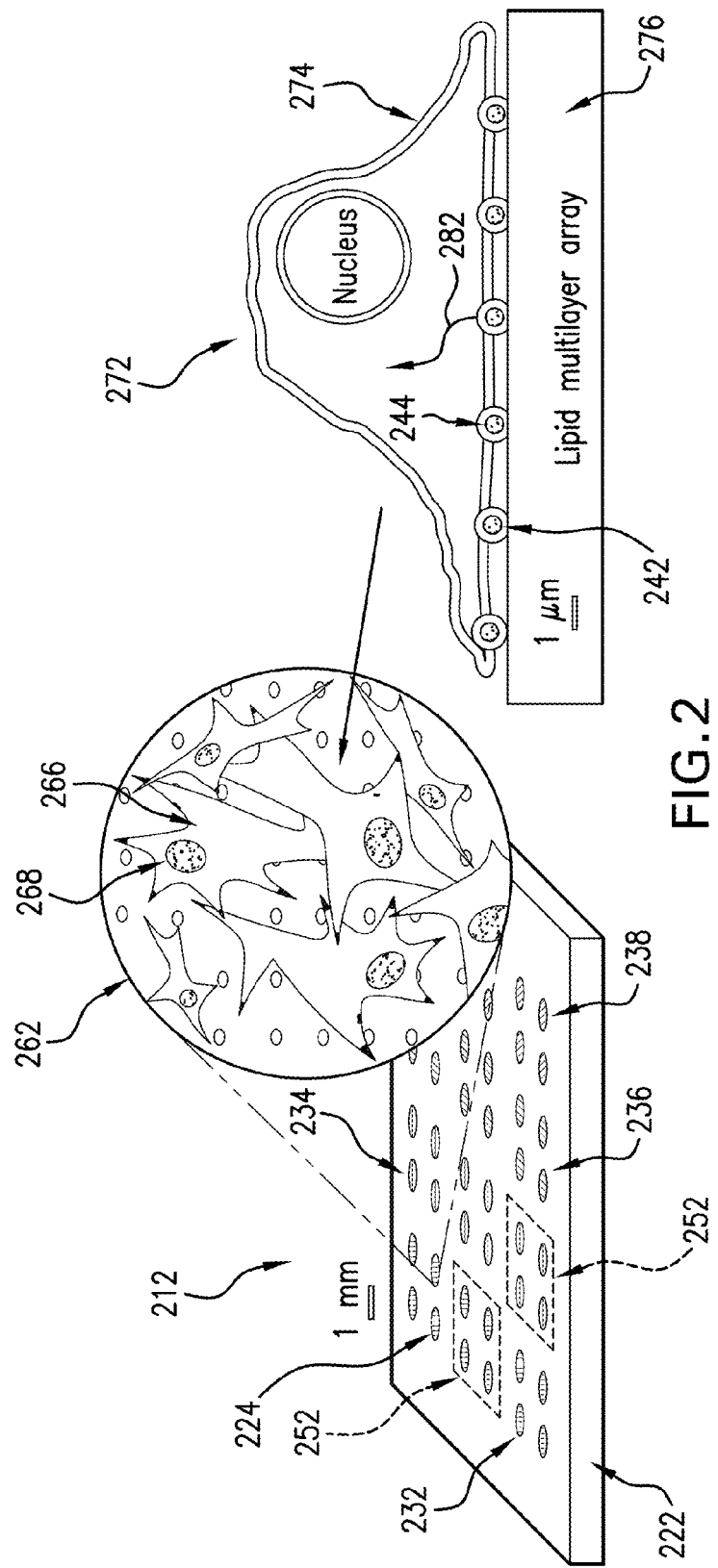
FIG. 2 is a schematic diagram showing a supported lipid multilayer microarray according to one embodiment of the present invention.

In one embodiment, the present invention provides surface-supported liposome arrays as a platform for screening of molecular libraries (e.g., drug efficacy) in cell culture models. Drug candidates encapsulated into surface-supported liposomes are arrayed on a surface to form lipid multilayer arrays using any one of several methods.[40,41,42,43] Cells are cultured on these arrays, and their response to the liposomes are monitored optically. Multiple liposome compositions (containing different drugs) and different lipids or other additives (e.g., to investigate delivery) printed onto the same surface can be screened simultaneously. Which drugs are and are not working can be determined by their position on the surface. An illustration of a supported lipid multilayer array according to one embodiment of the present invention is shown in FIG. 2. FIG. 2 shows a supported lipid multilayer microarray 212 according to one embodiment of the present invention. Supported lipid multilayer microarray 212 includes a substrate 222 having a lipid multilayer microarray 224 of lipid multilayer spots 232, 234, 236 and 238. Lipid multilayer spots 232, 234, 236 and 238 are each comprised of an array of lipid multilayer dots (liposomes) of which only lipid multilayer dots 242 of one lipid multilayer spot 232 are shown in FIG. 2. Encapsulated in dots 242 of lipid multilayer spot 232 are a first encapsulated material 244. Similarly, a second encapsulated material, a third encapsulated material and a fourth encapsulated material are encapsulated in the dots of lipid multilayer spots 234, 236 and 238, respectively. Lipid multilayer spots 232, 234, 236 and 238 are each arranged in groups of four, as shown by dashed boxes 252. Magnified circled region 262 shows a portion of a lipid multilayer spot of lipid multilayer spots 232 with cells 266 having nuclei 268 grown or deposited on lipid multilayer microarray 224. A schematic cross-sectional view 272 shows a cell 274 of cells 266 in contact with a group of dots 242 on a portion 276 of substrate 222. Arrow 282 shows an encapsulated material being delivered to cell 274 from a dot 242 by the process of endocytosis in which dots 242 are taken into cells 27.

Figure 3:
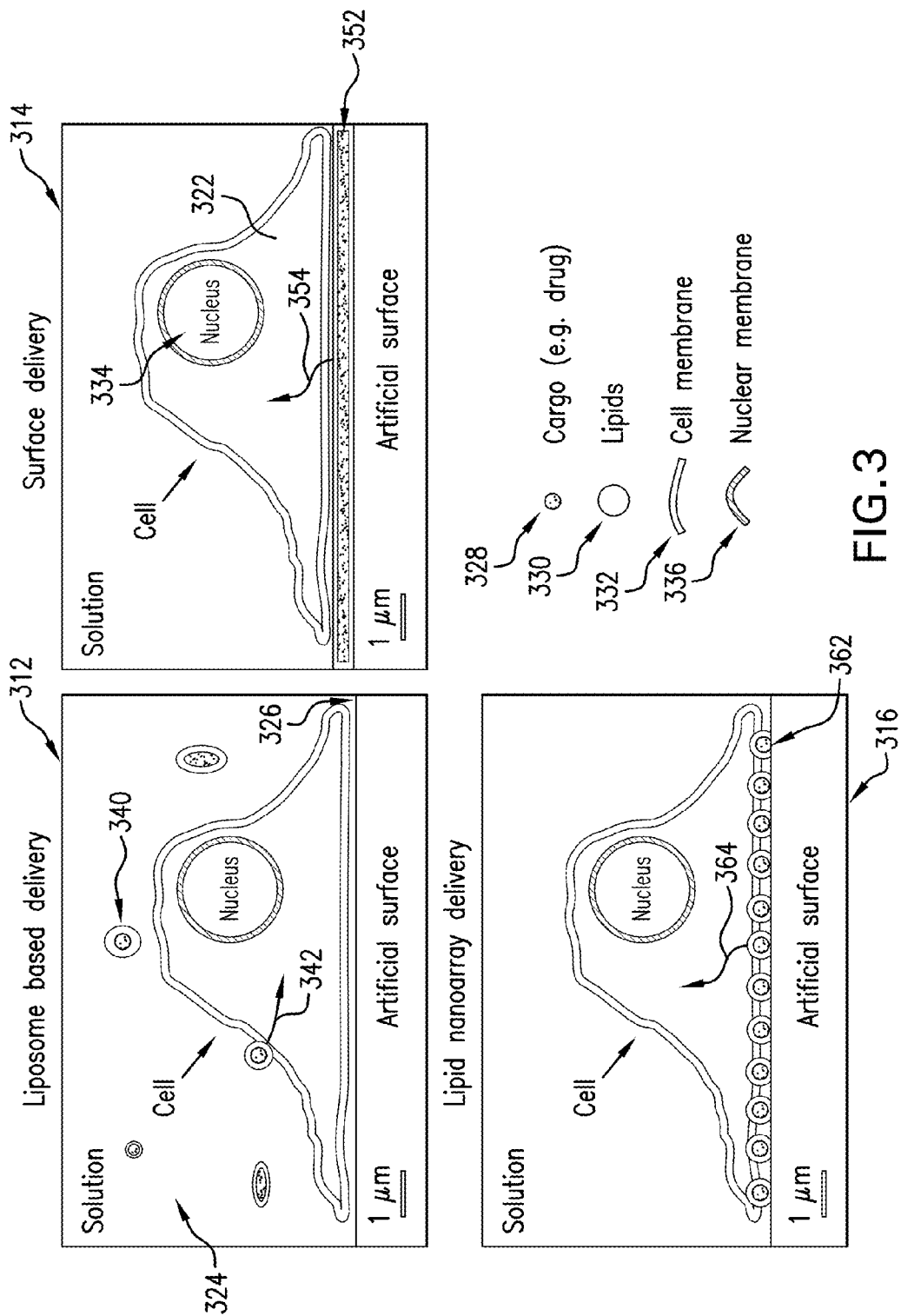
FIG. 3 is a diagram showing three drug delivery systems, including a lipid nanorray delivery system according to one embodiment of the present invention.

FIG. 3 shows three drug delivery systems: liposome based delivery (box 312), surface delivery (box 314) and lipid nanoarray delivery (box 316). All three drug delivery systems involve a cell 322, a solution (or in some embodiments a gas) 324, an artificial surface 326, a drug 328, lipids 330 and a cell membrane 332. Cell 322 includes a nucleus 334 having a nuclear membrane 336. In traditional liposome based delivery, lipids 330 in the form of liposomes in solution 340 may contact cell 322 held in place on artificial surface 326 and attach themselves to cell 322 thereby allowing drug 328 to enter into cell 322 by endocytosis in which the liposomes are taken into cell 322 as indicated by arrow 342. A problem with such a delivery system is that it is relatively random, with liposomes in solution varying in size and shape, and the dosage that each cell receives depending on diffusion of the liposomes in solution. Another problem with liposomal delivery from solution is that different cells in the same solution cannot receive different liposomal formulations in a controlled manner. In surface delivery, lipids 330 are present as a layer 352 on artificial surface 326. Drug 328 is delivered from lipids 330 in layer 352 to cell 322 as shown by arrow 354. A problem with surface delivery is only one liposomal formulation may be delivered at a time. Also the dose of the drug cannot be easily controlled. In lipid nanoarray delivery lipids 330 are present as lipid multilayer nanostructures 362 on artificial surface 326. Lipid multilayer nanostructures 362 are in contact with cell 322 thereby allowing drug 328 encapsulated in each lipid multilayer nanostructure 362 to be taken into cell 322 by endocytosis of each lipid multilayer nanostructure 362 as shown by arrow 364, allowing control of both dosage and the possibility to deliver different materials to different cells in the same solution or environment.

Although for simplicity of illustration in FIG. 3, the delivery of one drug is shown, in some embodiments of the present invention each lipid multilayer nanostructure could encapsulate a different drug, encapsulate a different dose of the same drug, etc.

Figure 4:
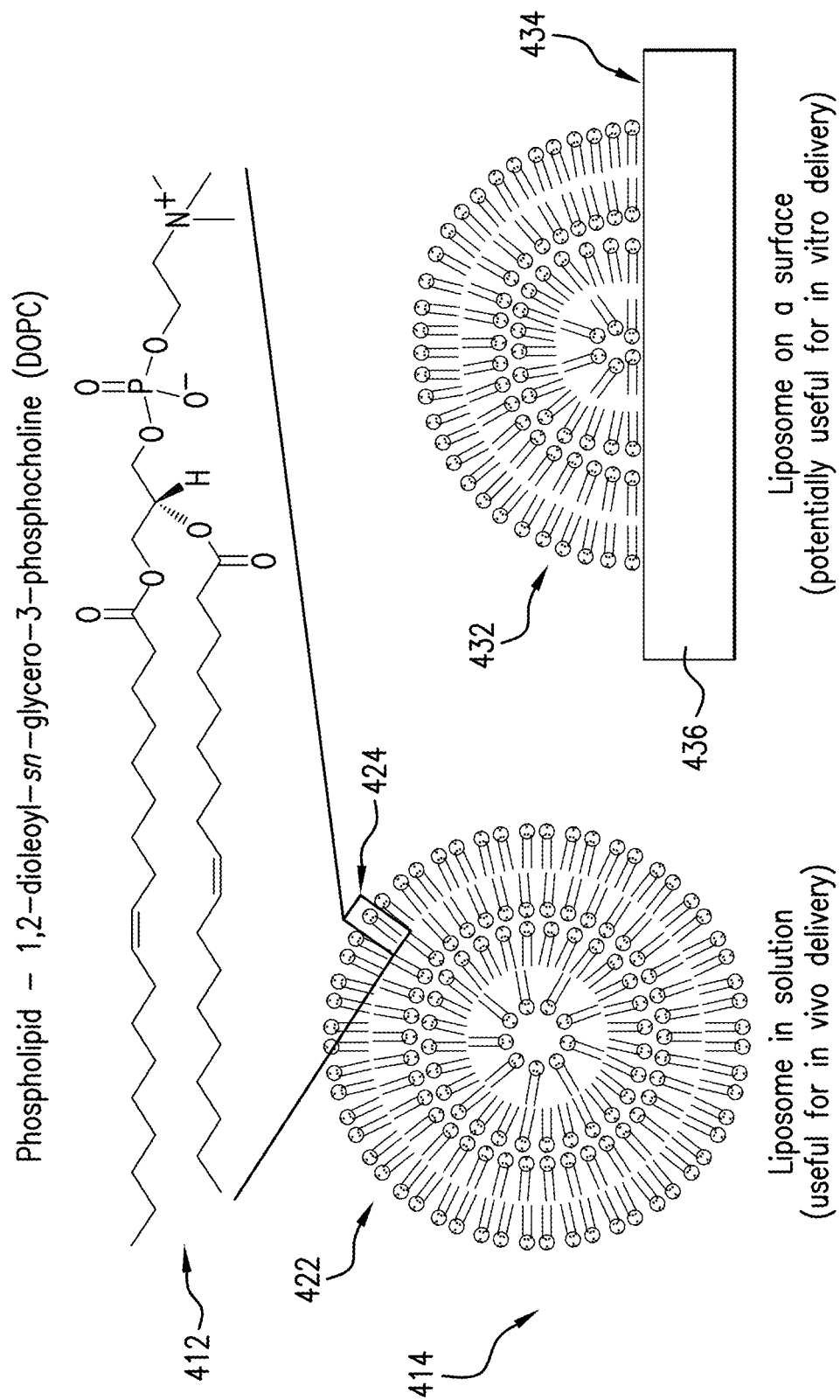
FIG. 4 is a diagram showing chemical and supramolecular structures of liposomes and surface-supported lipid nanostructures.

FIG. 4 shows chemical and supramolecular structures of liposomes and surface-supported lipid nanostructures. The chemical structure of 1,2-dioleoyl-sn-glycero-3-phosphocholine (DOPC), a typical phospholipid that may be used in lipid microstructure of the present invention, is indicated by arrow 412. FIG. 4 also shows example of one type of liposome supramolecular structure that self-assembles in water 414, i.e., multilamellar liposome 422 that is comprised of DOPC, as indicated by box 424. FIG. 4 also shows a surface-supported lipid multilayer liposome 432 on a surface 434 of a substrate 436. FIG. 4 shows one possible supramolecular structure and serves the purpose of comparing the structure of liposomes in solution with surface-supported liposomes or lipid multilayer nanostructures.

Figure 5:
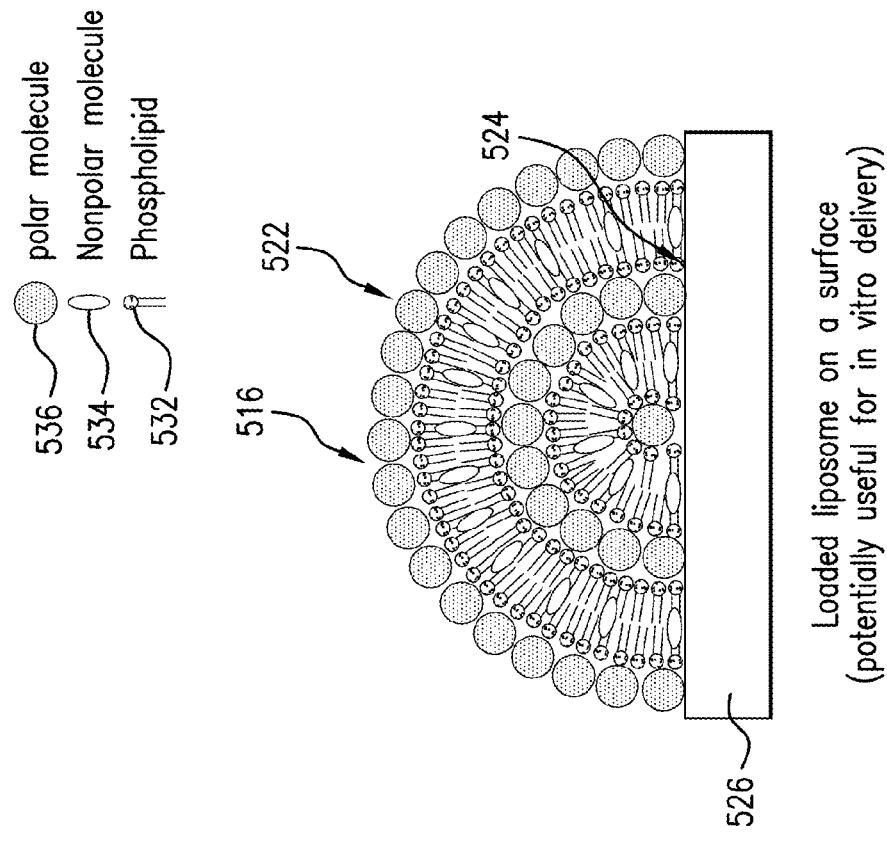
FIG. 5 is a diagram showing supramolecular structures of loaded liposomes and surface-supported loaded lipid nanostructures.
Figure 5:
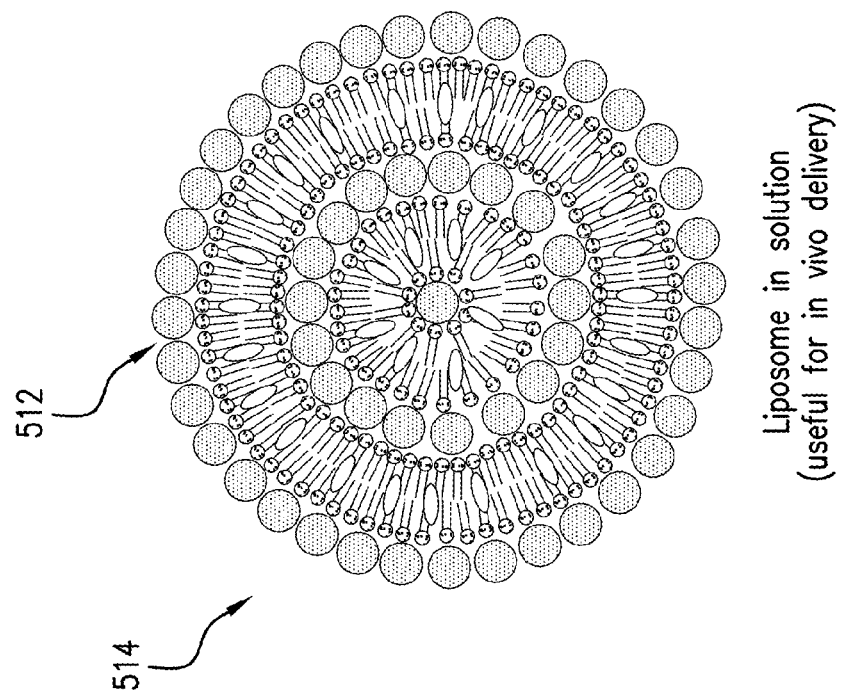
Figure 6:
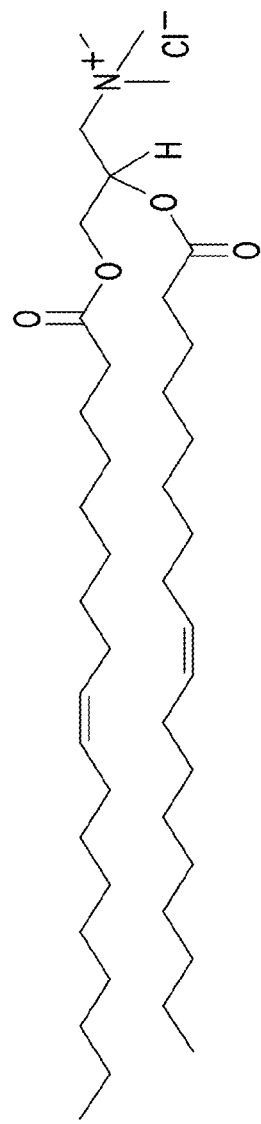
FIG. 6 shows the chemical structure of 1,2-dioleoyl-3-trimethylammonium-propane (chloride salt) (DOTAP).
Figure 7:
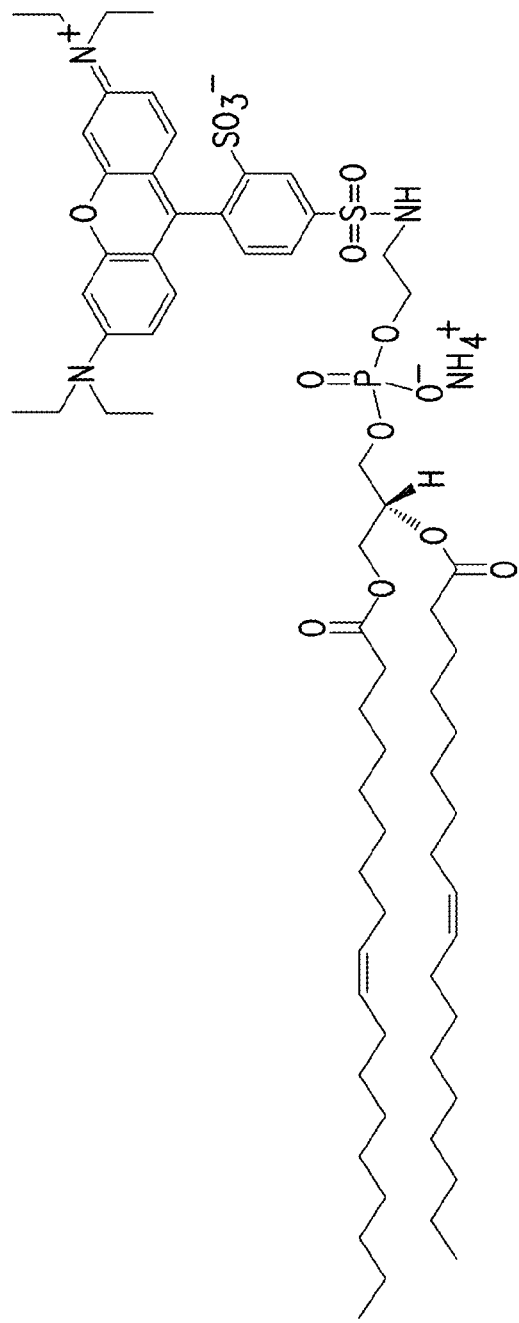
FIG. 7 shows the chemical structure of 1,2-dioleoyl-sn-glycerol-3-phosphoethanolamine-N-(lissamine rhodamine b sulfonyl) (ammonium salt) (DOPE-rhodamine).
Figure 8:
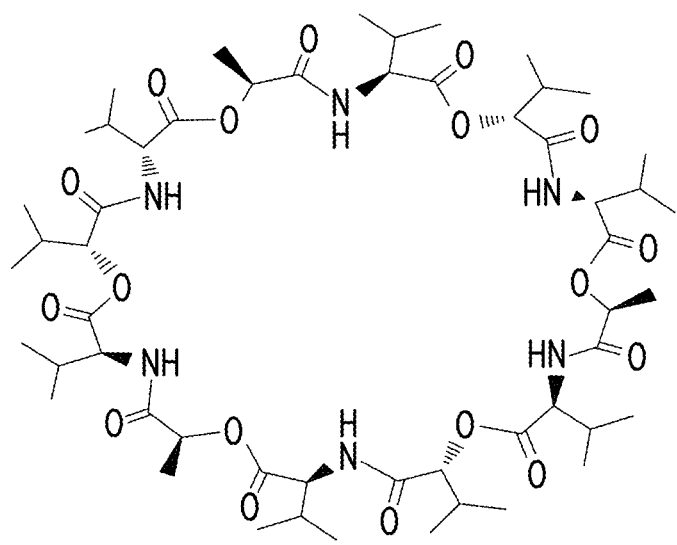
FIG. 8 shows the chemical structure of valinomycin.
Figure 9:
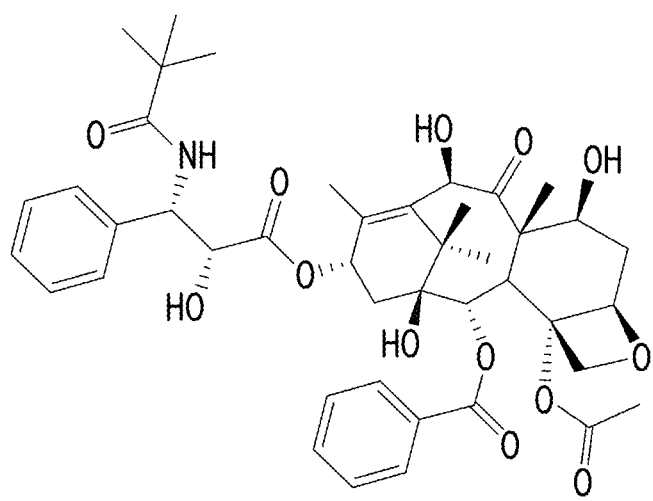
FIG. 9 shows the chemical structure of Taxotere® (docetaxel).

FIG. 5 shows supramolecular structures of a loaded liposome 512 in a solution 514 and a loaded surface-supported lipid nanostructure 516. Loaded surface-supported lipid nanostructure 516 comprises a loaded liposome 522 on a surface 524 of a substrate 526. Loaded liposome 512 and loaded surface-supported lipid nanostructure 516 are comprised of phospholipids 532, nonpolar molecules 534 and polar molecules 536. FIG. 5 shows possible locations of encapsulated materials within both solution-based liposomes and surface-supported liposomes or lipid multilayer nanostructures.

In one embodiment of the present invention, all or a portion of a lipid multilayer array may include various types of fluorescent additives to make the lipid multilayer structures of the array microstructure fluorescent. Examples of suitable fluorescent dyes include various fluorescent organic molecules, fluorescent proteins, pigments, nanoparticles, etc.

The substrate used in a lipid multilayer array of the present invention may be virtually any type of substrate on which lipid multilayer gratings may be deposited or grown, such as glass, plastic, paper, a semiconductor material, etc.

In one embodiment, dots or liposomes of the present invention may have lengths or widths between 100 nm to 5000 nm, and thicknesses between 10 to 200 nm.

EXAMPLES

Example 1

Materials and Methods
Materials

The chemical structures of the lipids and drugs used are shown in FIGS. 6, 7, 8 and 9. 1,2-dioleoyl-3-trimethylammonium-propane (chloride salt) (DOTAP) (FIG. 6) and 1,2-dioleoyl-sn-glycerol-3-phosphoethanolamine-N-(lissamine rhodamine b sulfonyl) ammonium salt) (DOPE-rhodamine) (FIG. 7) are purchased from Avanti Polar Lipids (700 Industrial Park Drive, Alabaster, Ala. 35007-9105, USA), as are all other lipids. Valinomycin (FIG. 8) was purchased from Sigma Aldrich LLC. Docetaxel was provided by Diego Zorio (Chemistry and Biochemistry Department, Florida State University. Poly-$_L$-lysine (FIG. 9) was purchased from Electron Microscopy Sciences (1560 Industry Road, Hartsfield, Pa., 19440, USA). A 16 LM 15 Torr 7.4 PSIG Vacuum Pump from KNF Lab is used for vacuum desiccation.

Preparation of Inks
Rhodamine Uptake Experiment

DOTAP is mixed with 1 mol % DOPE-rhodamine, and 2 µL was deposited in the M-type inkwell for the DPN 2000.

DOTAP/Valinomycin Ink

Powdered valinomycin is dissolved in chloroform at 20 mg/mL. DOTAP at 20 mg/mL is mixed with the dissolved valinomycin in a 4:1 lipid-to-drug ratio (lower ratios resulted in precipitation of the drug), and 2 µL of the mixture is deposited in each well of the inkwell. The chloroform is evaporated in a vacuum desiccator for 2 hours. The docetaxel ink is prepared in dimethyl sulfoxide (DMSO) at 20 mg/mL and is mixed with DOTAP in chloroform in a 1:4 drug-to-lipid mass ratio and deposited in the inkwell as described above. This ink is put in the vacuum desiccator at 30 mbar for 48 h before use for printing. This step is important because residual DMSO solubilizes the drug.

Glass Slide Preparation for Patterning

Glass coverslips are coated with poly-$_L$-lysine (0.1%) by incubating 500 µL of the solution on the coverslips at 37° C. in an incubator for 2 hours and then washing off the poly-$_L$-lysine with 5 mL of Millipore water. The coverslips are then air dried completely in a biosafety cabinet before use for printing.

Inking and Printing

Dip-pen nanolithography is carried out with the NLP 2000 machine from NanoInk (Skokie, Ill., USA). Inking is done with m-type tips at 80% relative humidity at room temperature for 30 min. The tips are moved periodically back and forth by about 5 µm during inking for maximum tip coating. The tip is first touched to the writing surface about 10 times for removal of the excess ink. The humidity is reduced to 40% while the tip is still in contact with the surface. Four-by-four dot patterns are made with 15-µm dot spacing and 35-µm pattern spacing.

Cell Culture

NIH 3T3 cells (obtained from the American Type Culture Collection, CRL-1658™, and maintained according to the collections guidelines) for all experiments are seeded at $4 \times 10^5$ cells/mL and grown to 70% confluence in Dulbecco's Modified Eagle Medium supplemented with 10% Cosmic Calf Serum (Sigma Aldrich). Trypsin (0.25%) is used for cell detachment, and the medium is replaced with fresh medium 24 hours before the experiment. Cells are seeded onto the patterned glass coverslips by gently pipetting a drop of the cell suspension directly over each pattern to prevent the patterns from being washed away. The same method is used to seed other parts of the slide for use as control areas. The cells are incubated over the patterned areas for 48 hours.

Solution Dose-Response
Rhodamine Dose-Response

Aliquots of DOPE-rhodamine (400 mL, 1 mg/mL) and DOTAP (400 mL, 50 mg/mL) in chloroform are prepared in a glass amber tube and mixed. The lipids are serially diluted with chloroform to produce five solutions with DOPE-rhodamine masses of 0.02, 0.2, 2, 20 and 200 mg. The chloroform is evaporated in a gentle stream of nitrogen gas. Residual chloroform is removed under vacuum for 2 hours. To form liposomes, 100 mL of Hank's buffered salt solution is gently added and incubated for 20 min; 200 mL of media is then added to each of the resulting solutions and further incubated for 5 min. NIH 3T3 cells plated the previous day in 6-well plates at 70% confluence are washed, and 1.7 mL of new medium is added to each well. The formulations are then added to these wells. After 48 hours, the cells are washed with TBS buffer, new medium is added and fluorescence imaging is done.

Valinomycin Dose-Response

Aliquots of valinomycin (20 mg/mL) and DOTAP (20 mg/mL), both dissolved in chloroform, are placed in an amber glass vial and serially diluted to produce valinomycin masses of 20, 10, 5, 2.5, 1.25 and 0.63 mg. Drying, liposome formation and cell culture are conducted as described above for the Rhodamine dose-response. Toxicity assays are performed after 24 and 48 hours.

Docetaxel Dose-Response

Docetaxel (20 mg/mL) dissolved in DMSO is further serially diluted in Hank's buffered salt solution to produce seven solutions with docetaxel masses of 50, 25, 12.5, 6.25, 3.2, 1.6 and 0.8 mg respectively, each with a total volume of 100 mL. The eighth is a solution of DMSO only (control) at the same volume as the 50 mg solution. These mixtures are added to 200 mL of medium and added to the cells in the same manner as described above for the Rhodamine dose-response. Toxicity assays are performed after incubation for 48 hours.

Dose-Response Curve Analysis

Data are plotted with Origin 8.1. The following sigmoidal function is used to fit the dose-response curve:

$$A1 + \frac{(A2 - A1)}{(1 + 10^{(LOGx0 - \log(x)) \cdot p})}$$

where A1=the bottom asymptote, A2=the top asymptote, LOGx0=the center, and p=the Hill slope.

Cell Viability Assay

The BacLight live/dead assay is purchased from Invitrogen. The cells are incubated with both SYTO 9 and propidium iodide for 20 min. The cells stained with both are counted as dead, and those stained with SYTO 9 only are counted as live.[34,35] All counting of live and dead cells is done by hand.

Microscopy

Microscopy for all the imaging except the supplementary video is done with a Nikon Eclipse Ti microscope. The printed patterns and the Retiga-SRV fast 1394 camera are used. Patterns are imaged in brightfield before cell culture. Nikon fluorescence filter sets B-2E/C FITC and G-2E/C TRITC are used for the live/dead cell assay. Imaging is done at 800 m sec exposure time with the 10× (NA=0.3) objective and at 1 second for the 4× (NA=0.13) objective. Lamp intensity for all imaging is set at 4. Microscopy for the live cell lipid uptake for the supplementary video is done with a Nikon TE-2000-E inverted microscope equipped with a Nikon Plan Apo 40× (NA=0.95) DIC objective.

Statistics

ANOVA tables are calculated with the Excel® statistical analysis tool. p-values represent the probability of a significant difference between the means of the samples with $\alpha=0.05$. The mean values are taken from triplicate samples. Error bars on graphs represent standard deviation.

Results

Controlled Uptake from Surface

Figure 10:
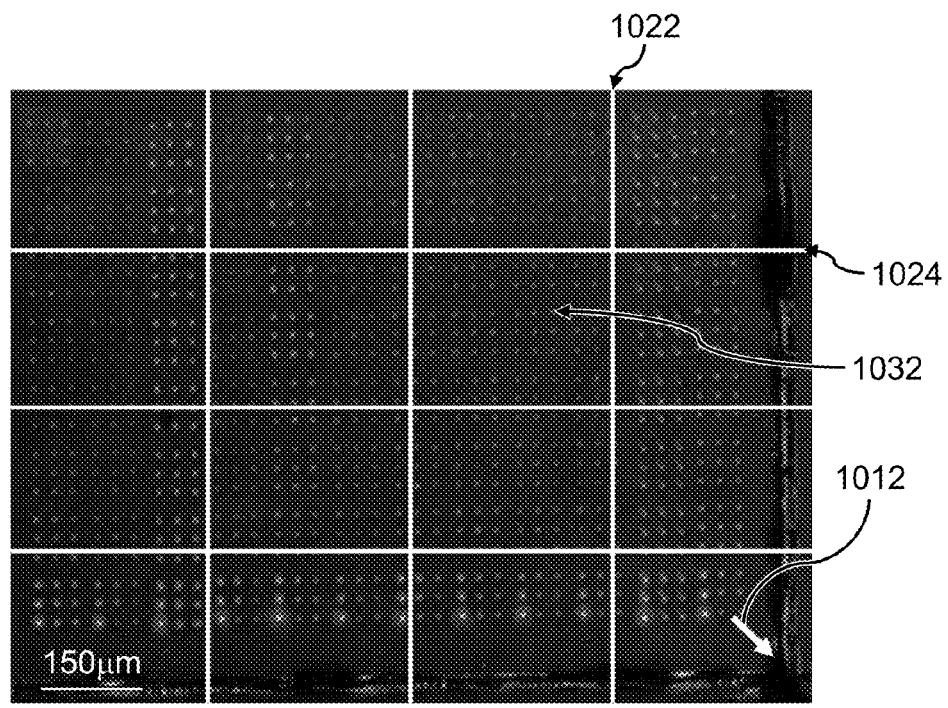
FIG. 10 is a merged image of phase contrast and fluorescent images of a rhodamine-labeled phospholipid DPN pattern before cell culture for a sample.
Figure 11:
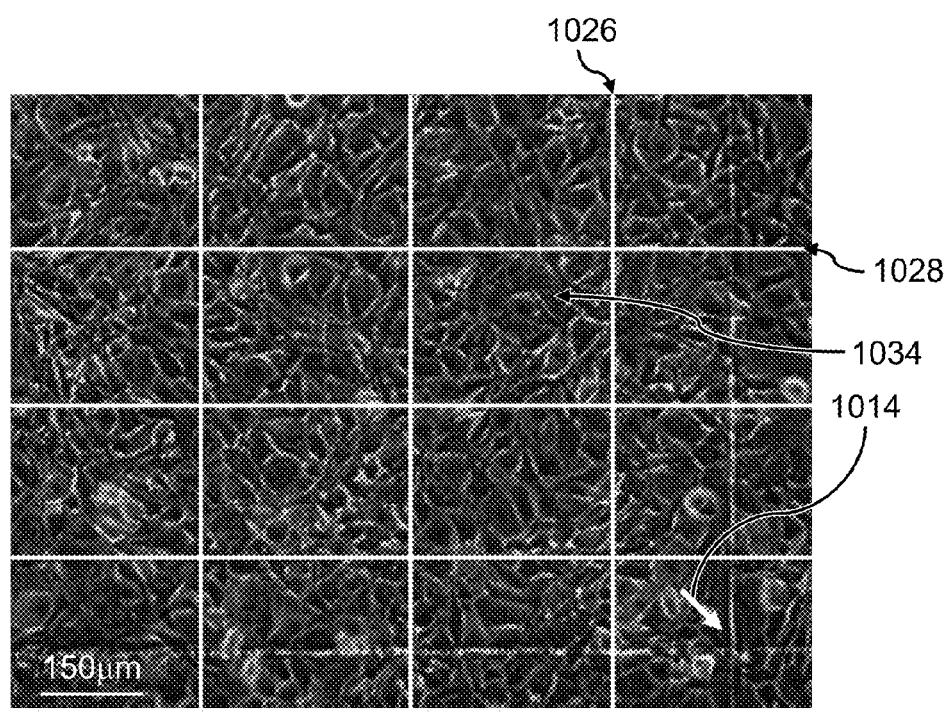
FIG. 11 is an image of cells after incubation over the pattern in FIG. 10 for 18 hours for the sample of FIG. 10.
Figure 12:
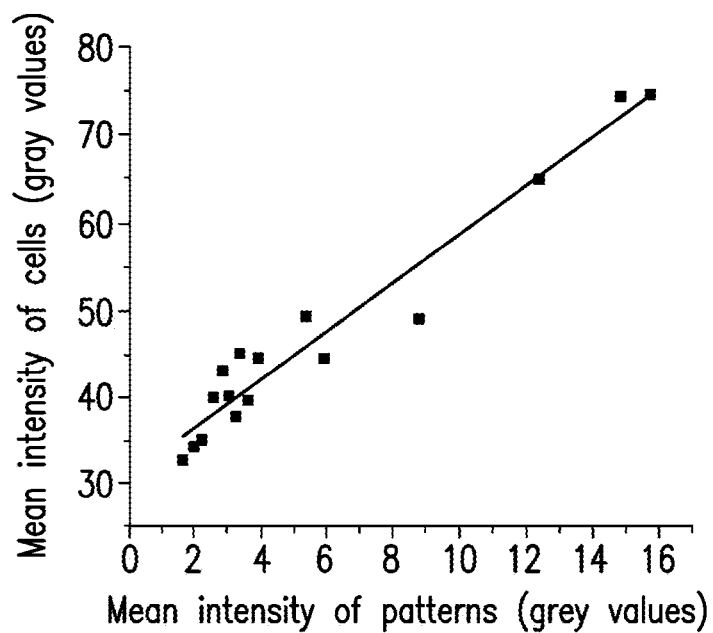
FIG. 12 is a graph showing an analysis of the correlation of intensity of spots with the average intensity of the cells for the sample of FIG. 10.
Figure 13:
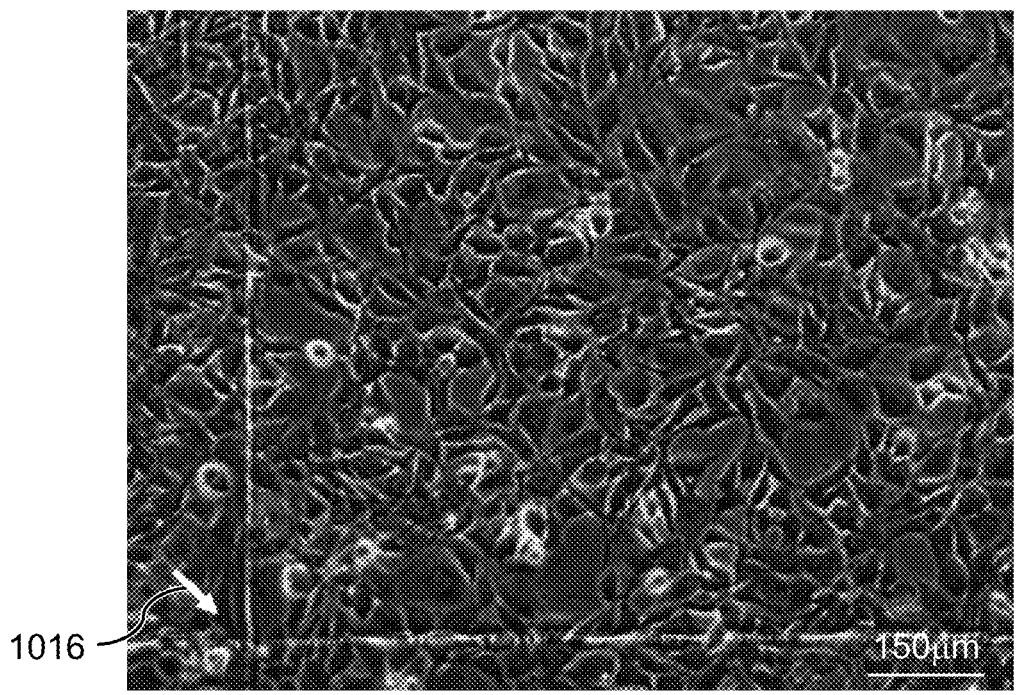
FIG. 13 is an imaging showing cells residing in a region immediately to the right of the region shown FIG. 11.
Figure 14:
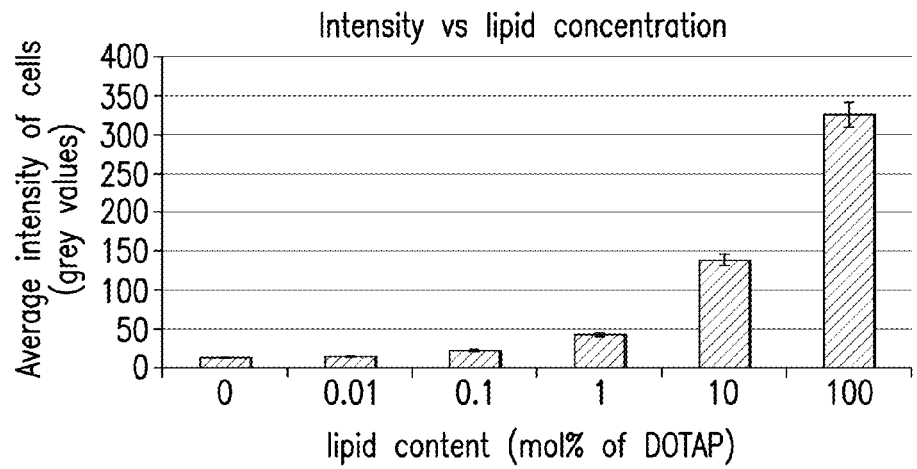
FIG. 14 shows the concentration-dependent uptake of lipids from solution by the cells of the sample of FIG. 10.
Figure 15:
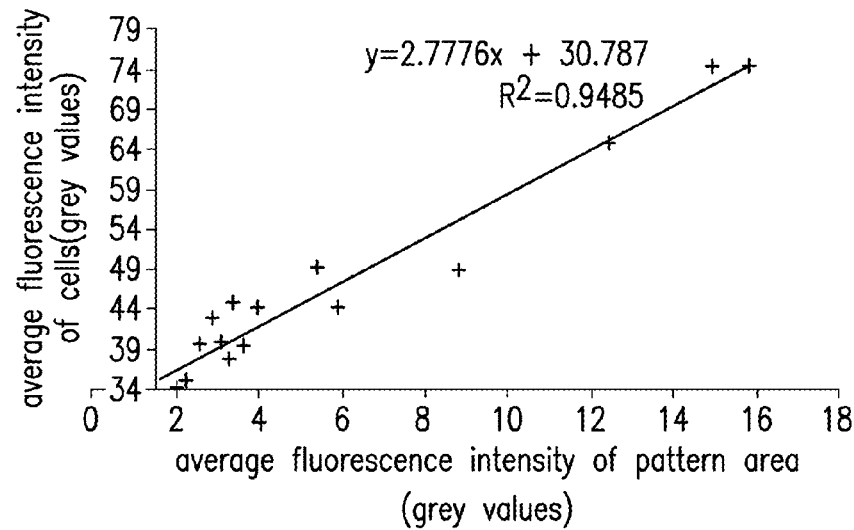
FIG. 15 shows an ImageJ analysis of the correlation of intensity of dots with the average intensity of the cells of the sample of FIG. 10.

To demonstrate and quantify lipid uptake by the cells, NIH 3T3 cells are cultured over a rhodamine-doped lipid multilayer pattern for 24 hours, see FIGS. 10, 11, 12, 13, 14 and 15. FIGS. 10, 11, 12, 13, 14 and 15 show the uptake of DOPE-rhodamine-labeled DOTAP by NIH 3T3 cells. FIGS. 10, 11 and 13 are all images from the same sample, and arrows 1012, 1014 and 1016 indicate common alignment marks that are scratched on the glass coverslips. FIG. 10 is a merged image of phase contrast and fluorescent images of a rhodamine-labeled phospholipid DPN pattern (array) before cell culture. FIG. 11 is an image of cells after incubation over the pattern in FIG. 10 for 18 hours. Fluorescence intensity is used as the indicator of the amount of lipid taken up by the cells. A higher fluorescence in cells indicates higher uptake of lipids. Grid lines 1022 and 1024 in FIG. 10 and grid lines 1026 and 1028 in FIGS. 10 and 11 divide the images of FIGS. 10 and 11 into areas 1032 and 1034, respectively, analyzed and compared for fluorescence intensity before and after cell incubation on the patterns. This division provided the highest correlation of the fluorescent intensities of the patterns with those of the cells, suggesting that this area is the average distance the cells migrated during the experiment. FIG. 12 is a graph showing an analysis of the correlation of intensity of dots with the average intensity of the cells. Images are divided into equal areas as seen in FIGS. 10 and 11 using grid lines 1022 and 1024 in FIG. 10 and grid lines 1026 and 1028 in FIG. 11 for determination of the localization of the cells to their sources of lipids. The linearity of this relation indicates the possibility of obtaining dose-response curves from a single area of an array. The cells over the dots with high fluorescence intensity took up the most lipids and showed the highest intensity. FIG. 13 shows that cells residing in a region immediately to the right of the region shown FIG. 11 do not fluoresce. The contrast of images has been adjusted in the look-up tables of the NIKON NIS software for viewing purposes only. FIG. 14 shows the concentration-dependent uptake of lipids from solution by the cells. FIG. 15 shows an ImageJ analysis of the correlation of intensity of dots with average intensity of the cells (ImageJ is a public domain, Java-based image processing program developed at the National Institutes of Health).

The lipids are taken up by the cells (FIG. 11) over the patterned area but not by those over the area immediately beside the pattern (FIG. 12). The data indicate that the lipids did not dissolve or disperse into the aqueous solution and diffuse to surrounding cells under culture conditions before being absorbed. In addition, the larger spots delivered more lipids to the cells than did the smaller spots, as revealed when the patterned area is divided into 250 μm×250 μm sections (grid lines 1022 and 1024 of FIG. 10 and grid lines 1026 and 1028 of FIG. 11) and the correlation between the fluorescence intensity of the original spots and the fluorescence intensity of the cells in the same area after cell culture is plotted (FIG. 11). This area is chosen because it provided the best correlation between the fluorescence intensity of the areas before and after cell culture, suggesting that the cells did not migrate beyond this area.

To determine the rate of DOPE-rhodamine uptake by the cells, live cell imaging is performed with cells cultured over a lipid pattern for 25 hours, which provided an indication of the time scale of lipid uptake by the cells. Spots without cells maintained their fluorescence intensity while those beneath cells are absorbed, producing an increase in fluorescence intensity of the cells. The fluorescence of the absorbed spots begins to decrease sharply after 20 hours and had completely disappeared by 25 hours, so that a 5-hour window is the critical uptake time. This uptake rate is important, because it reveals the minimum incubation time before any assays can be performed on the cells when drugs are delivered. The fluorescence intensity of areas around the arrays and cells (within 100 mm) is quantified over time.

Lipid-Mediated Drug Delivery

Figure 16:
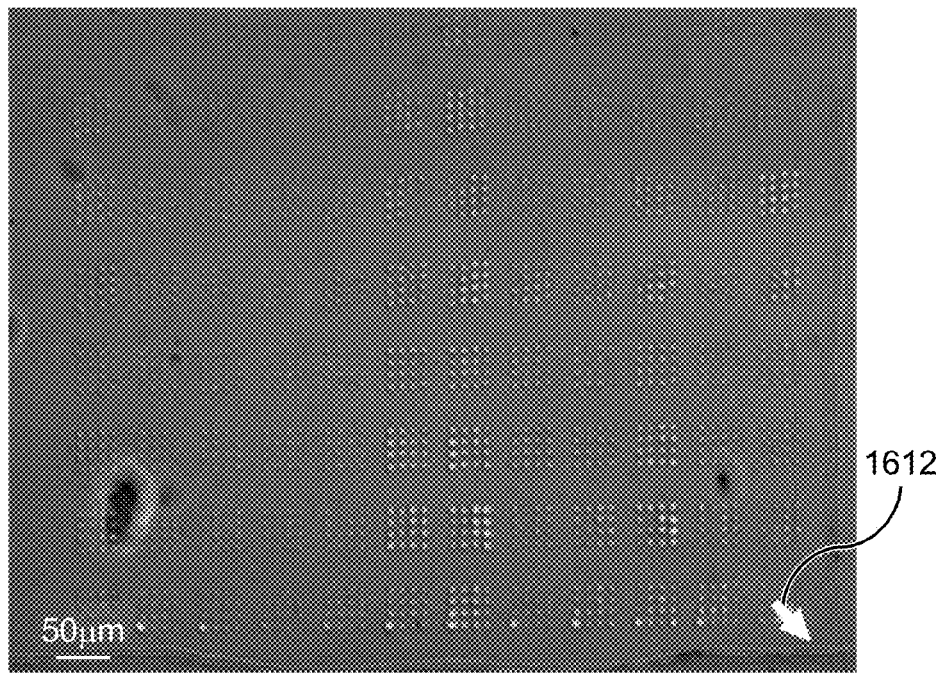
FIG. 16 is a brightfield image of a DOTAP/valinomycin pattern before cell culture for an assay.
Figure 17:
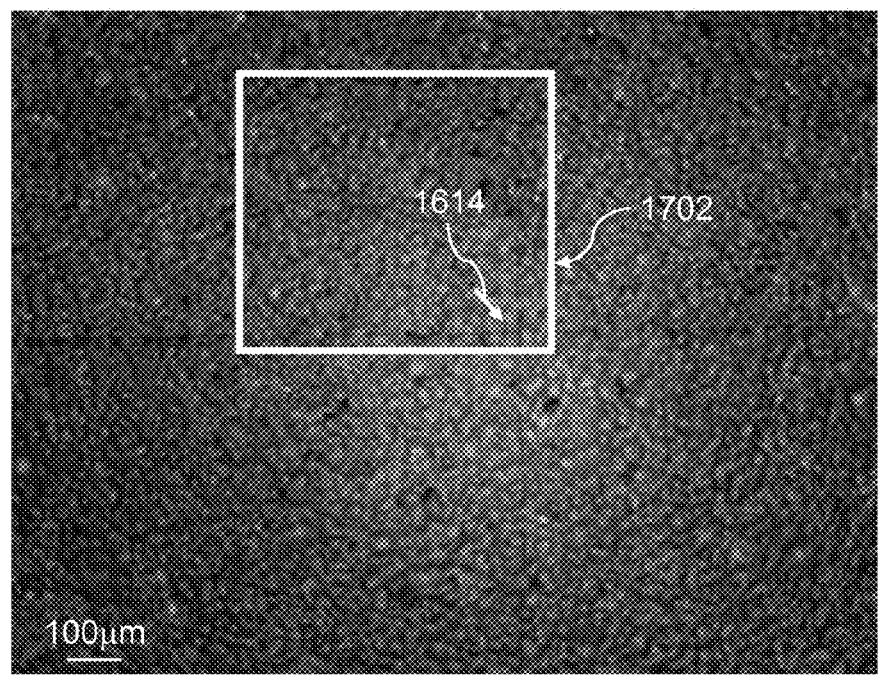
FIG. 17 is a 4× image of a live/dead assay of cells for the assay of FIG. 16.
Figure 18:
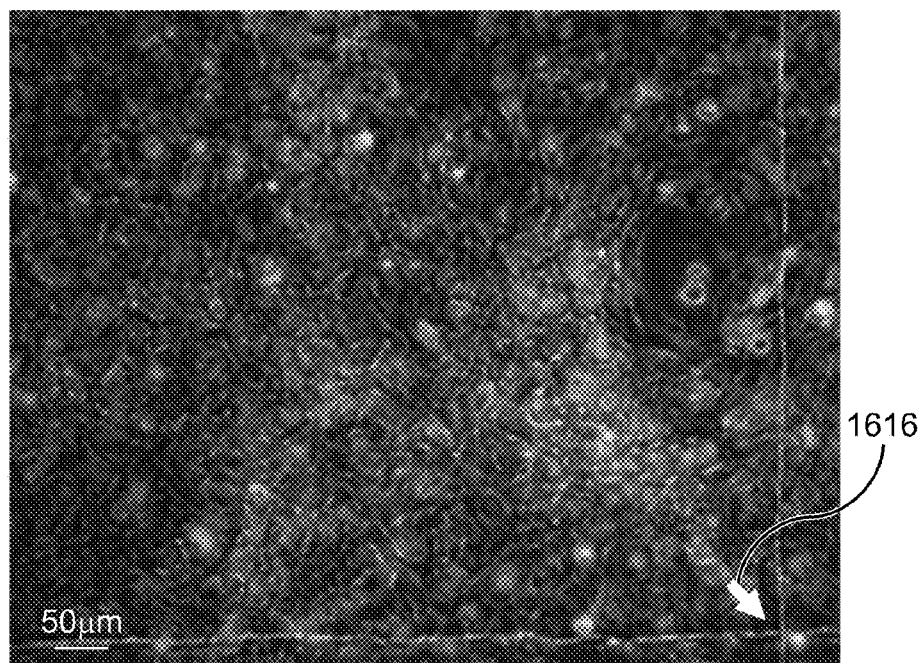
FIG. 18 is a higher magnification of a highlighted square area of FIG. 17 for the assay of FIG. 16.
Figure 19:
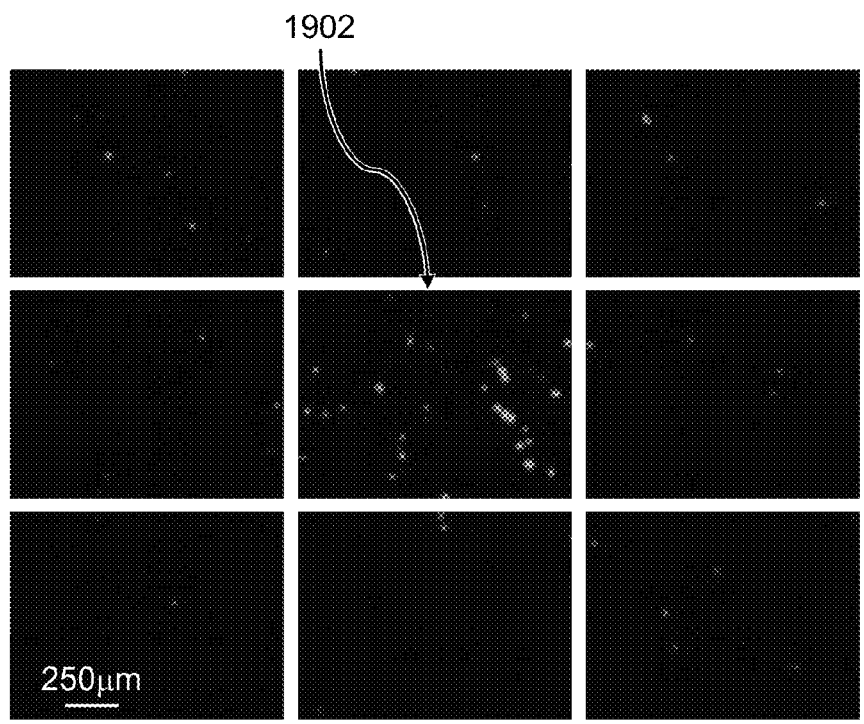
FIG. 19 is a mosaic of images (TRITC filter set) for the assay of FIG. 16.

Valinomycin is tested first because of its quick action as a cytotoxic agent and immediate action upon incorporation into the cellular membrane. The drug acts as a potassium ionophore, facilitating loss of potassium and resulting in cell death. FIGS. 16, 17, 18 and 19 show a toxicity assay of cells that are cultured over a lipid multilayer microarray. In the assay of FIGS. 16, 17, 18 and 19, valinomycin is delivered to cells from a lipid multilayer microarray as revealed by a toxicity assay. In FIGS. 16, 17 and 18, arrows in 1612, 1614 and 1616 point to the same alignment mark. FIG. 16 is a brightfield image of DOTAP/valinomycin pattern before cell culture. FIG. 17 is a 4× image of a live/dead assay of cells (square area 1702 shows area with patterns). FIG. 18 is a higher magnification of the square area 1702 of FIG. 17. Images are taken after 24 hours. Images in FIGS. 17 and 18 are the merged TRITC and FITC fluorescence channel images. FIG. 19 is a mosaic of images (TRITC filter set). Central square 1902 corresponds to FIG. 17, and the other squares are the areas immediately surrounding central square 1902. All live cells are stained green; nuclei of dead cells are stained red.

Comparison of dose-response curves of liposomal valinomycin delivered from solution with those of cells exposed to the DOTAP/valinomycin pattern revealed a toxicity level from the surface of about 11%, which corresponds to a concentration of about 0.1 mg/mL from solution. This value is significantly different from that of the controls without the drug ($p<0.05$). To determine whether the lipid/drug mixtures are sufficiently localized to affect only the cells over the patterned areas, the viability of cells from areas surrounding the pattern (measured from immediately beside, up to 2000 mm away from the pattern) is compared to that of the cells directly over the pattern. The two differ significantly ($p<0.05$).

Simultaneous Multidrug Surface Delivery

To demonstrate simultaneous multidrug delivery, the drugs Taxotere® (docetaxel) and valinomycin are used. Taxotere® (docetaxel) is an anticancer drug and is a second-generation, semisynthetic analog of Taxol® (paclitaxel). Taxanes, which include paclitaxel and docetaxel, work by binding to microtubules and stabilizing them, thus preventing their disassembly and progression through mitosis, and therefore their functioning inside the cytoplasm. The cell may revert to the G1 phase or undergo apoptosis.[36] Cells are plated over patterns (such as that in FIG. 16) consisting of lipid only, lipid-encapsulated docetaxel and lipid-encapsulated valinomycin, all on the same glass coverslip and incubated for 48 hours. The results are shown in FIGS. 20, 21, 22, 23, 24, 25, 26, 27, 28 and 29.

Figure 20:
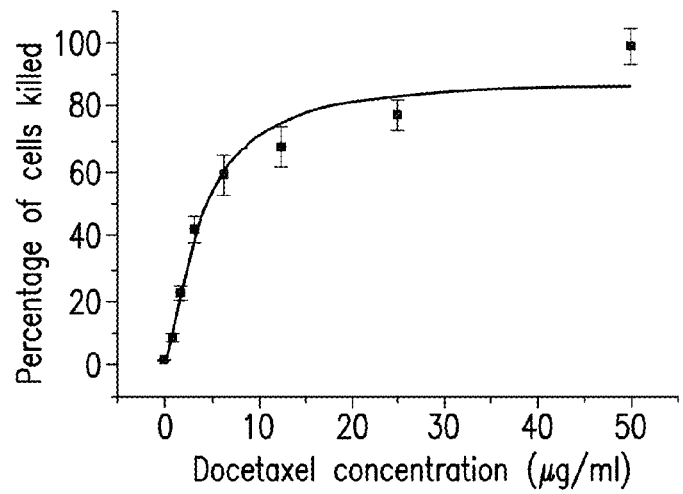
FIG. 20 is an image showing the dose-response assay of Taxotere® (docetaxel) delivered from a solution with DOTAP.
Figure 21:
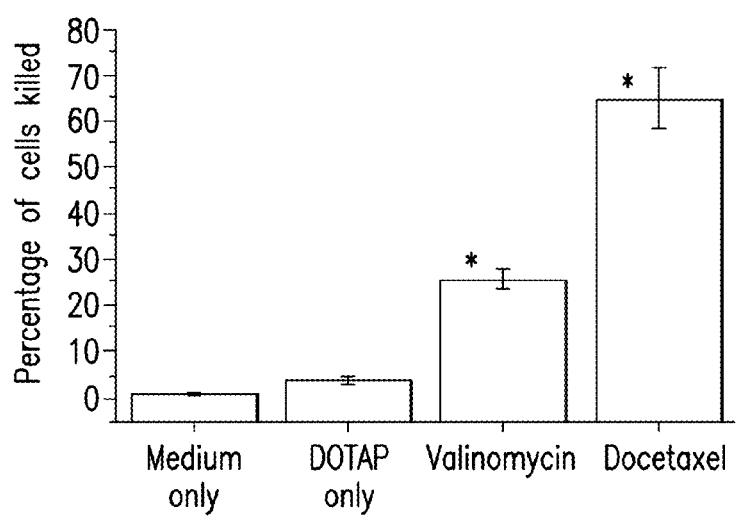
FIG. 21 is a graph showing the percentage of cells killed over each drug pattern area for the dose-response assay of FIG. 20.
Figure 22:
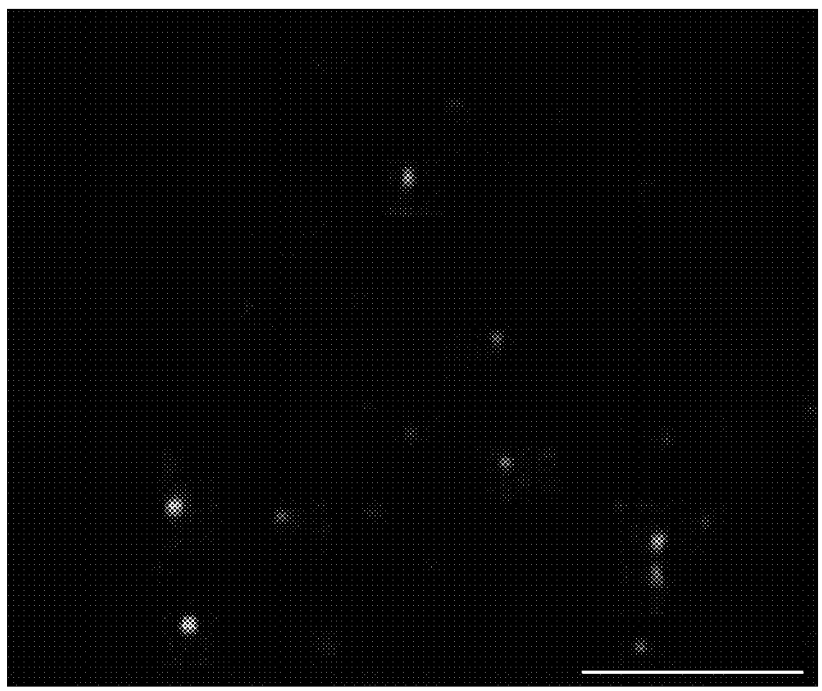
FIG. 22 is an image of cells over an area away from the patterns, which serves as a first control (TRITC filter set) for the dose-response assay of FIG. 20.
Figure 23:
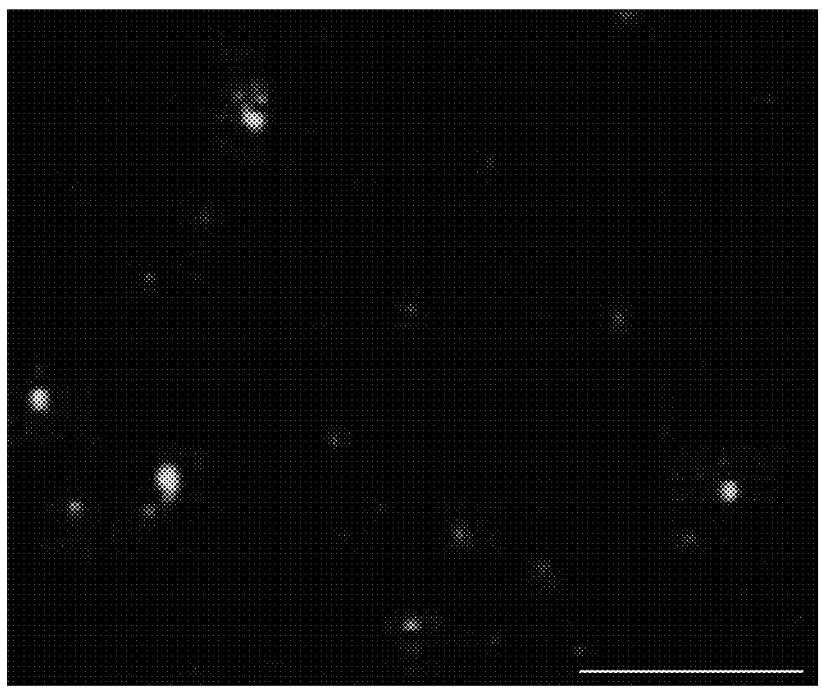
FIG. 23 is an image of cells over a DOTAP pattern used as a control for the dose-response assay of FIG. 20.
Figure 24:
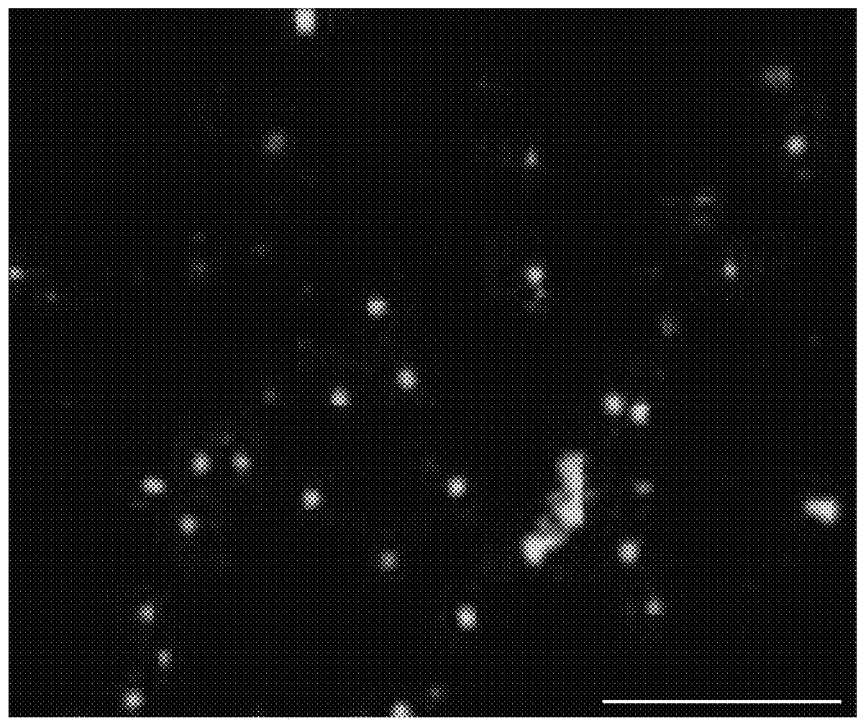
FIG. 24 is an image of cells over areas having a valinomycin pattern.
Figure 25:
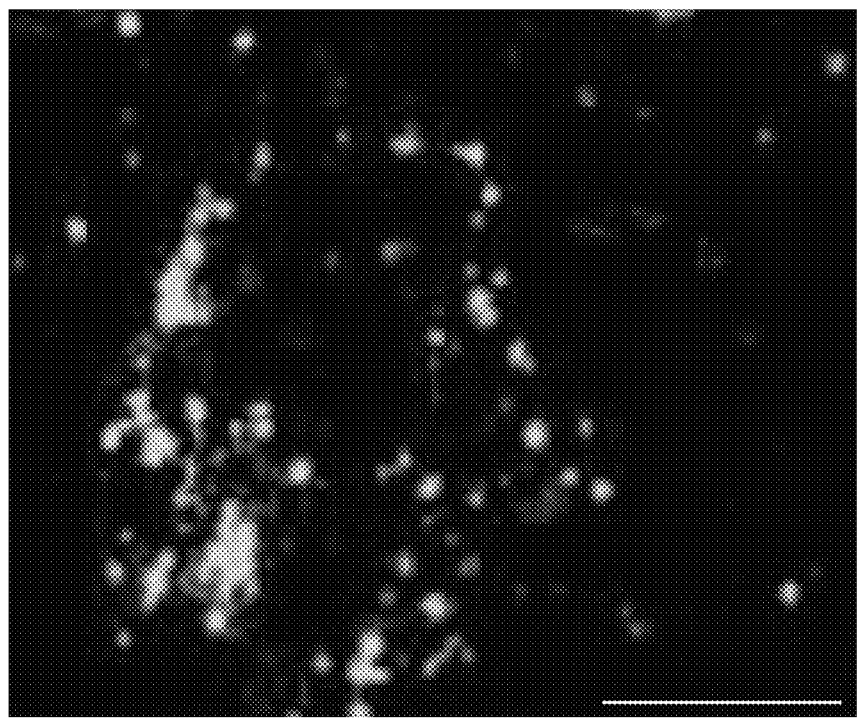
FIG. 25 is an image of the cells over areas having a docetaxel pattern.
Figure 26:
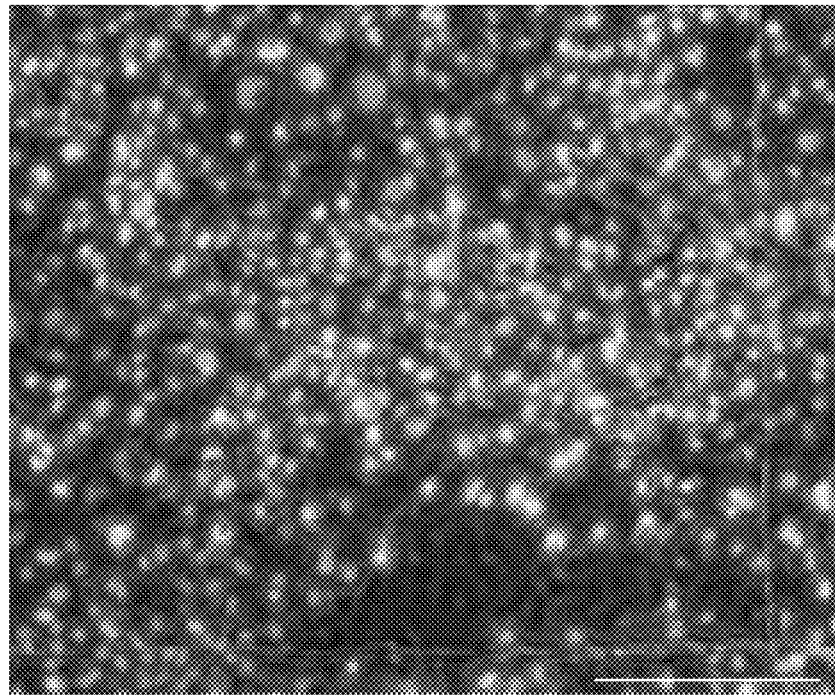
FIG. 26 shows the merged FITC, TRITC and phase contrast image of FIG. 22.
Figure 27:
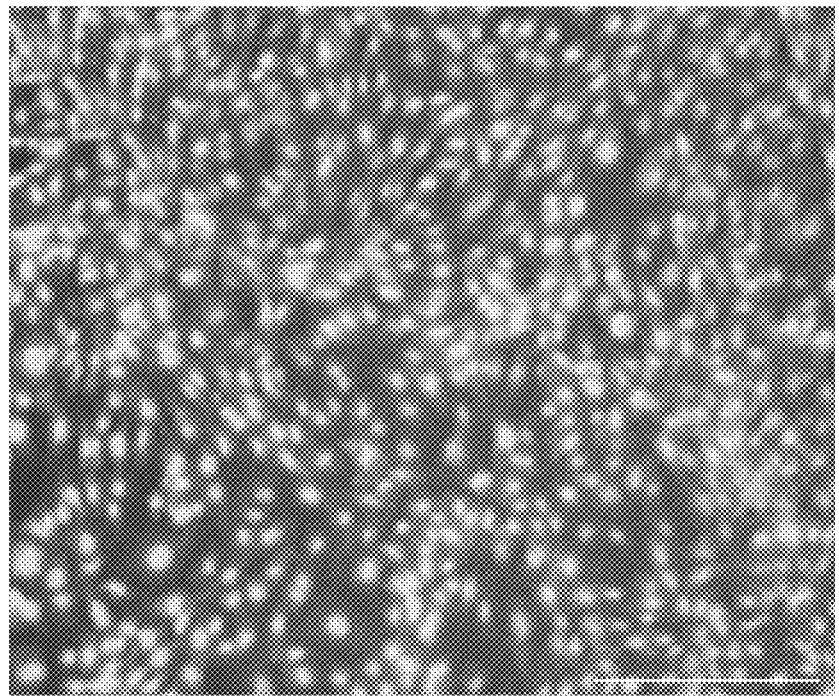
FIG. 27 shows the merged FITC, TRITC and phase contrast image of FIG. 23.
Figure 28:
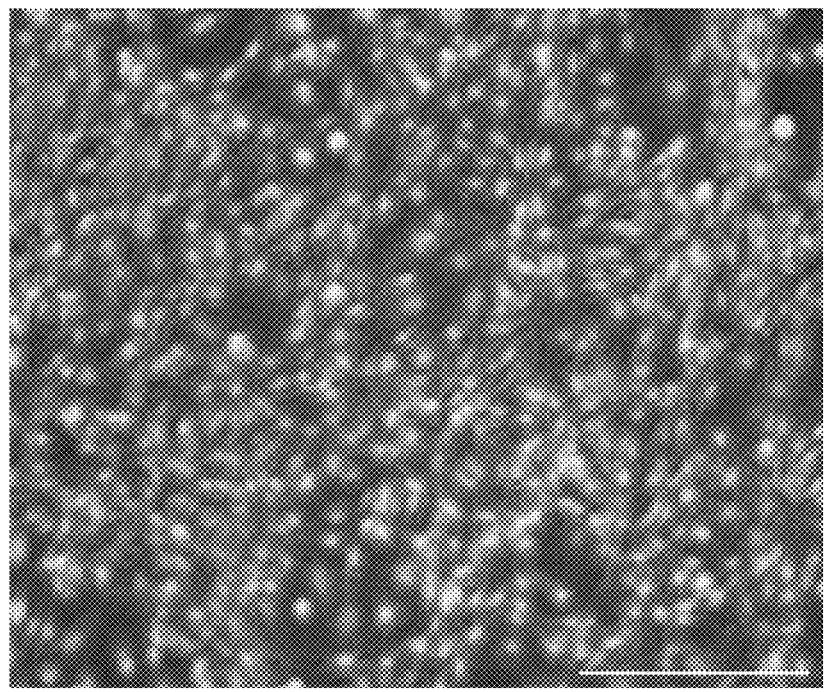
FIG. 28 shows the merged FITC, TRITC and phase contrast image of FIG. 24.
Figure 29:
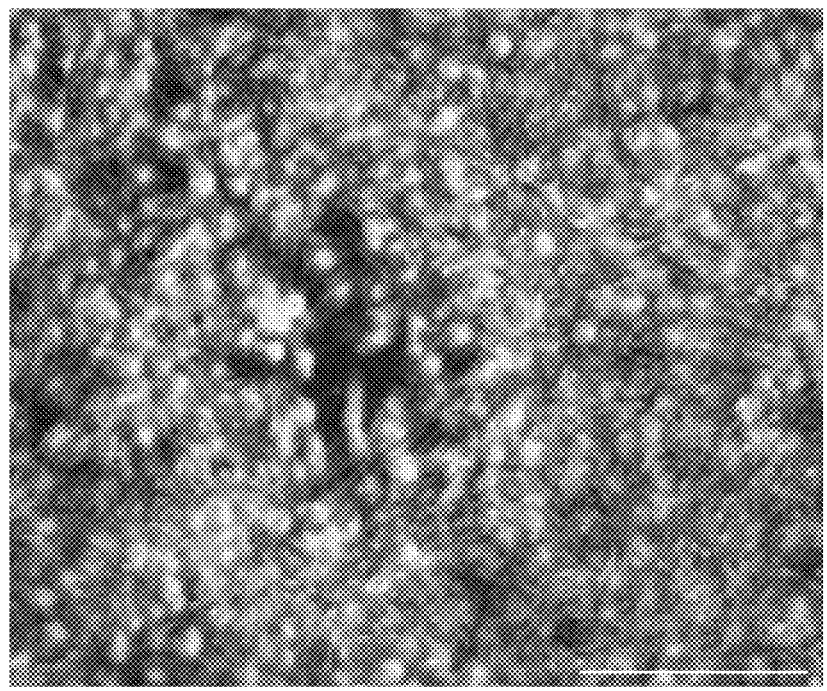
FIG. 29 shows the merged FITC, TRITC and phase contrast image of FIG. 25.

FIG. 20 shows the dose-response of Taxotere® (docetaxel) delivered from solution with DOTAP. FIG. 21 shows the percentage of cells killed over each drug pattern area. FIG. 22 is an image of cells over an area away from the patterns, which serves as a first control (TRITC filter set). FIG. 23 is an image of cells over a DOTAP pattern used as a control. FIGS. 24 and 25 are images of the cells over areas with valinomycin and docetaxel patterns. FIGS. 26, 27, 28 and 29 show the merged FITC, TRITC and phase contrast images of FIGS. 22, 23, 24 and 25, respectively. The live/dead assay is used, and cells are cultured for 48 hours.

In FIGS. 22, 23, 24, 25, 26, 27, 28 and 29: 1. All cells are stained green, whereas only nuclei of dead cells are stained red. 2. Error bars on graphs are standard deviation in triplicate samples on different glass coverslips. 3. A significant difference from the control (medium only) is denoted by an asterisk "*". 4. Scale bars=250 µm.

The docetaxel pattern produced over 60% cell death, and the valinomycin produced about 25% cell death (FIG. 21). Longer incubation of the valinomycin pattern, for 48 hours, produced an increase in cell death over that shown in FIGS. 16, 17, 18 and 19, which corresponded to incubation for 24 hours. The intervening space between the patterns (FIGS. 22 and 26) is compared to a control with medium only and to patterns with DOTAP only in order to eliminate toxicity due to the lipid. The toxicities from the DOTAP pattern did not differ significantly from that of the control with medium only (FIG. 21; p>0.05). The figure also shows that docetaxel produced a much higher toxicity in the cells than did valinomycin. This toxicity is comparable to that achieved by approximately 6.25 mg/mL of the docetaxel dissolved in DMSO delivered from solution. An important consideration here is to produce cellular uptake over the pattern only and not in the surrounding area. This aspect is essential to establishing that the drugs do not dissolve into solution or spread with the lipids to affect cells on other areas of the surface. Confining the lipids to multilayered drops rather than allowing them to spread quickly into monolayers potentially keeps the drugs at high enough concentrations to be effective against the cells. In addition, the retardation of spreading allows for enough space between the drops to provide adhesion points for cells. These spaces, coupled with poly-$_L$-lysine's property of promoting cell adhesion, will further increase cell adhesion, especially for less-adherent cells.

Discussion

On the assumption that about 100 cells are sufficient for testing of an individual compound or dosage, the method described here should be scalable such that $10^5$-$10^6$ dosages and/or drugs could be tested on the area of a single standard microtiter plate. DPN provides a method of rapid prototype fabrication by directly depositing many different materials onto surfaces with high lateral resolution and arbitrary pattern-generation capabilities and, in the case of lipids, control of multilayer thickness.[29,32] An advantage of using phospholipids is their immiscibility with water, which is crucial to preventing cross-contamination in an aqueous environment. It is expected that hydrophobic drugs will be located predominantly in the hydrophobic portions of the lipid multilayer. Being embedded in the hydrophobic portion protects the drugs from dissolution until they are taken up by the cells. Preventing cross-contamination allows for separation of drug arrays without wells, permitting compatibility of this method with existing cell culture methods—a lipid multilayer array can be printed directly into a microwell plate.

Even without cross-contamination, the issue of cell migration must be considered, as a cell might pick up one drug or volume, then migrate to a neighboring area and pick up another. This possibility is controlled for by seeding cells at a high enough density to produce at least a 70% confluence to limit migration by contact inhibition. Also, the incubation time is limited to 24-48 hours for the assay. If more motile cells (such as some cancer cells) or longer culture times are desirable, a structured surface containing migration barriers could be used to prevent cell migration between neighboring patterns.[37] The box sizes in FIG. 11 (~250 µm wide) are found to be optimal for obtaining a dose-response curve in which the cells do not migrate farther than the dimensions of the boxes. Spacing between the individual spots sufficient to allow for cell adhesion with the substrate is also crucial, as the cells do not adhere to lipid multilayer dots that are larger than the cells (image not shown). Therefore the use of dots smaller than the cells is necessary for this method.

This example demonstrates the ability to control the dosage that a cell receives using fluorescently labeled phospholipids (FIGS. 10, 11, 12 and 13) by correlating the fluorescence intensity of the spots to the fluorescence intensity of cells cultured on different sized spots. Fluorescence intensity of the spots is proportional to multilayer height, and it has recently been shown that this can be used for high-throughput quality control.[38] Different wavelength fluorophores may be used to obtain dose-response curves for the drug delivery or a label-free method of determining lipid multilayer height, such as optical profiling, dark-field microscopy, profilometry or atomic force microscopy may be employed. Technical challenges also remain in scaling up DPN for integrating thousands of different compounds onto the same array.[39] One promising approach is lipid multilayer stamping, which has been recently developed as an alternative method for the fabrication of lipid multilayer arrays.[40] This method uses a microarrayer to deliver liposome mixtures to a structured polymer stamp, which is then used to print the lipids onto the surface, resulting in subcellular lateral resolution, control of multilayer thickness, and higher throughput and homogeneity of multilayer thickness than those of DPN.[40]

Another technical issue is the stability of the lipid multilayer arrays upon immersion into water. Although lipids have negligible solubility in water, on certain surfaces lipid multilayers will spread to form a monolayer or bilayer, and fluid lipids can be disrupted upon crossing the air-water interface when being immersed in water. The spreading problem may be solved by using a polylysine surface on which the lipids do not spread to form a single bilayer. The immersion problem is solved by careful addition of the medium to the chip, but it has also been shown elsewhere that immersion can be addressed by application of the solution in the absence of humidity (e.g., in a nitrogen atmosphere), where the lipids are in a gel phase.[29] The lipid multilayer array method of drug delivery is therefore a simple way to deliver different drugs simultaneously to cells on prefabricated microarray plates without the necessity for separate chambers for each combination. It therefore allows more assays per unit area than do microtiter plates. In addition, lipid multilayer arrays require smaller amounts of drugs (femtograms/screen) and reagents or cells (the equivalent of one plate could do what currently requires 1000 plates). In addition to the drug discovery application, the low number of cells required could make this method suitable for screening drugs on primary cells, for example those obtained from patient biopsies, for determination of efficacy for personalized medicine.

Conclusion

The above experiments demonstrate the suitability of lipid multilayer microarrays for local delivery of small-molecule drugs to cultured cells at dosages comparable to solution based delivery (the equivalent of 30 mg/mL) without any observable uptake by neighboring cells. The results of the above experiments demonstrate that the dot size-dependent lipid uptake can control the dosage of these phospholipids to cells. The results of the above experiments further demonstrate that two drugs incorporated into separate phospholipid (DOTAP) patterns about 1000 mm apart on the same slide are specifically delivered to cells in contact with the patterns without cross-contamination of other cells on the slide. These results demonstrate that a single high-throughput screening microarray plate may be used in the same way as a standard well plate.

Example 2

Figure 30:
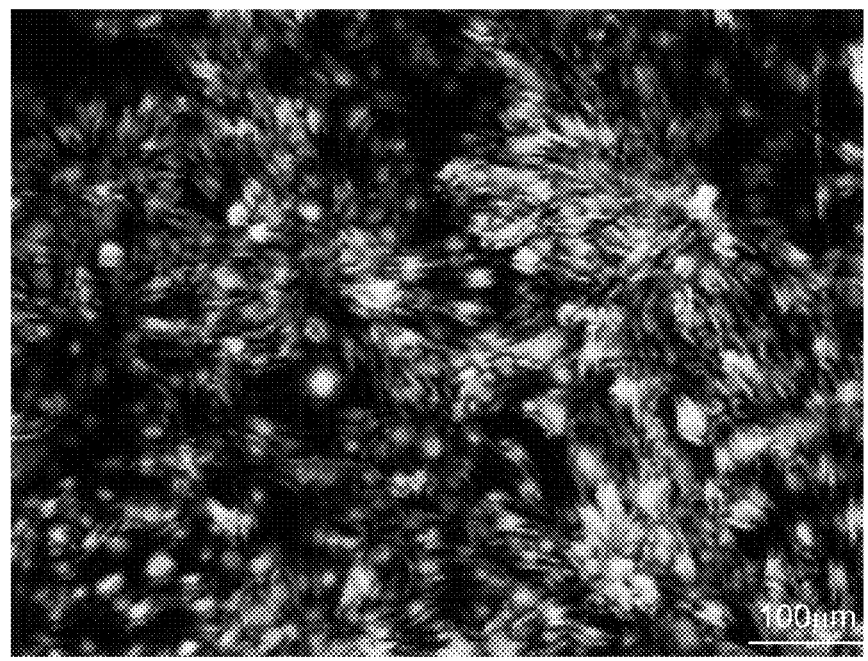
FIG. 30 is an image of a cytotoxicity assay showing the ability of the anticancer drug Taxotere® to kill NIH 3T3 cells from the surface of the lipid multilayer array according to one embodiment of the present invention.
Figure 31:
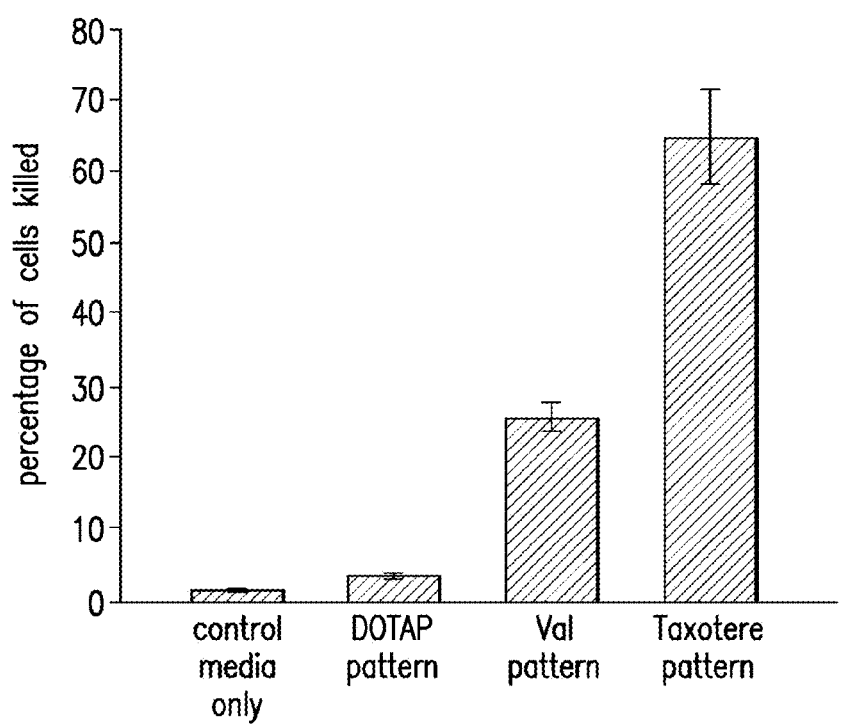
FIG. 31 is a bar graph of the percentage of cells killed for DOTAP, valinomycin (val) and Taxotere® delivered from a lipid multilayer array, according to one embodiment of the present invention compared to a control.

An assay of cytotoxicity of anticancer drugs delivered from a lipid multilayer array to cells on the surface of the array is conducted. These drugs include DOTAP, valinomycin and docetaxel (Taxotere®). The cells include cancerous and noncancerous cell lines. In the case of cancer drugs, toxicity to cancer cells is a measure of efficacy. FIGS. 30 and 31 show an experiment in which two different liposomal drug compositions as well as controls without the drug are tested on the same surface. FIG. 30 is an image of a cytoxicity assay showing the ability of the anticancer drug Taxotere® to kill NIH 3T3 cells from the surface of the lipid multilayer array. FIG. 31 is a bar graph of the percentage of cells killed (cytotoxicity) for DOTAP, valinomycin (val) and Taxotere® delivered from a lipid multilayer array according to one embodiment of the present invention compared to a control.

Example 3

Figure 32:
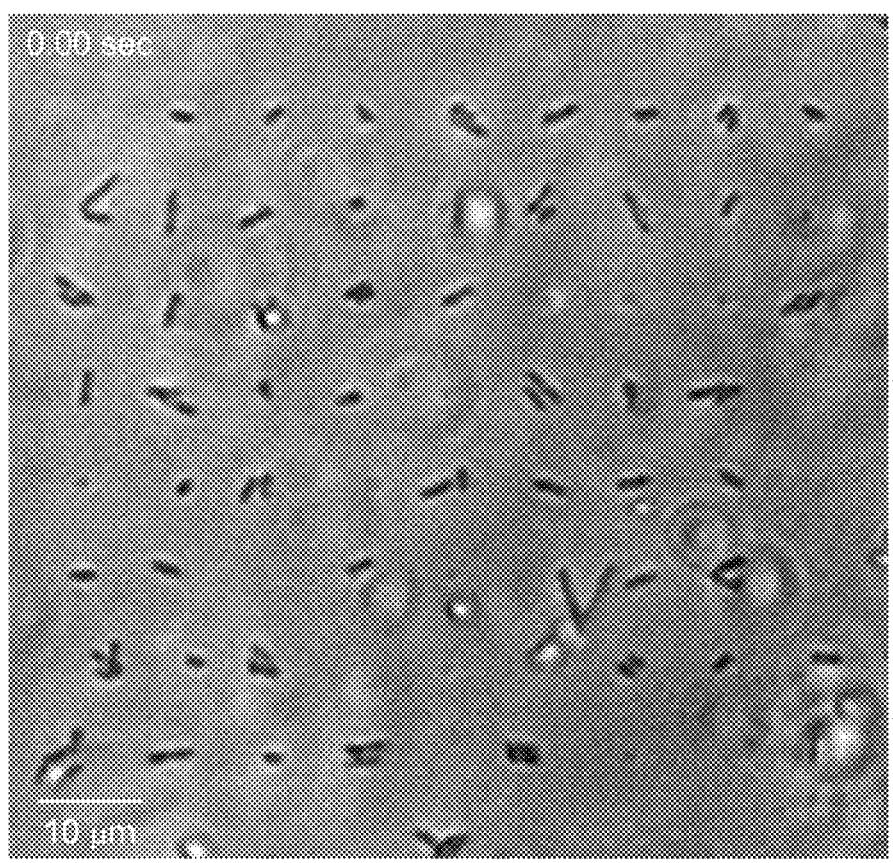
FIG. 32 is an image showing selective adhesion of *Escherichia coli* bacteria to a lipid multilayer microarray.

Bacteria are selectively adhered to lipid multilayer microarrays. FIG. 32 shows selective adhesion of *Escherichia coli* bacteria to a lipid multilayer microarray, indicating the possibility of using the present invention for screening of material interaction with prokaryotic cells, for instance for screening of antibiotic efficacy.

Example 4

Figure 33:
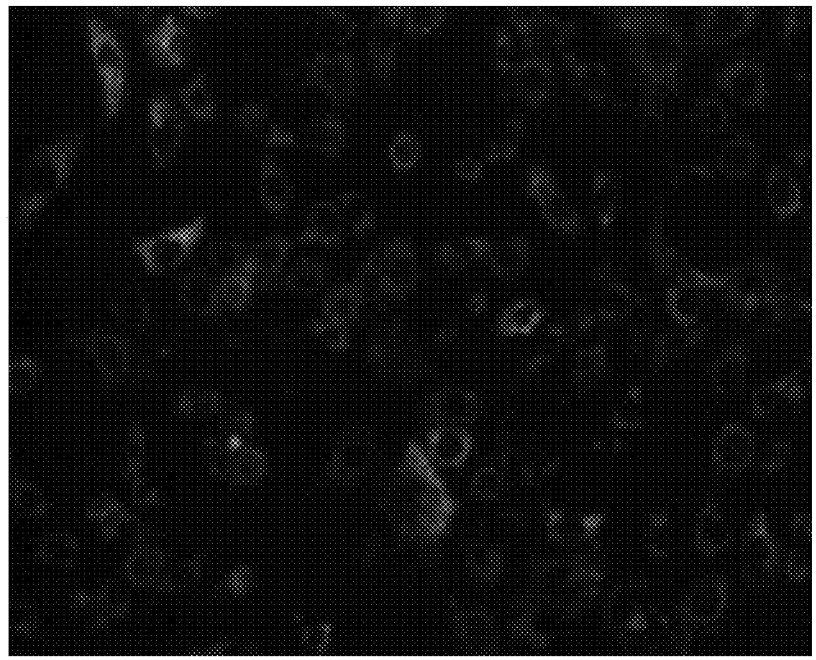
FIG. 33 shows a fluorescence image of the uptake of the fluorophore (fluorescent molecule) rhodamine from a solution of liposomes composed of 1 mol % rhodamine.
Figure 34:
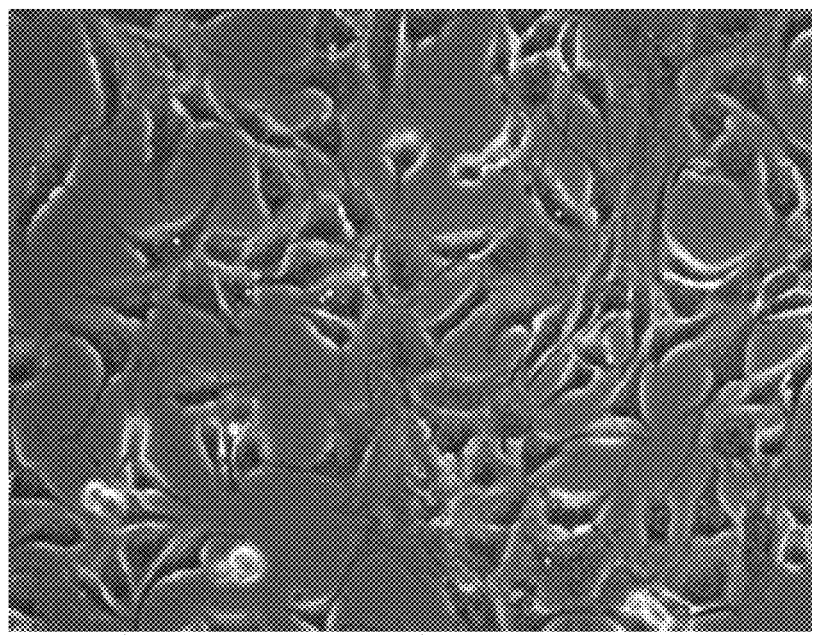
FIG. 34 shows a brightfield image of the uptake of rhodamine by the cells of FIG. 33.
Figure 35:
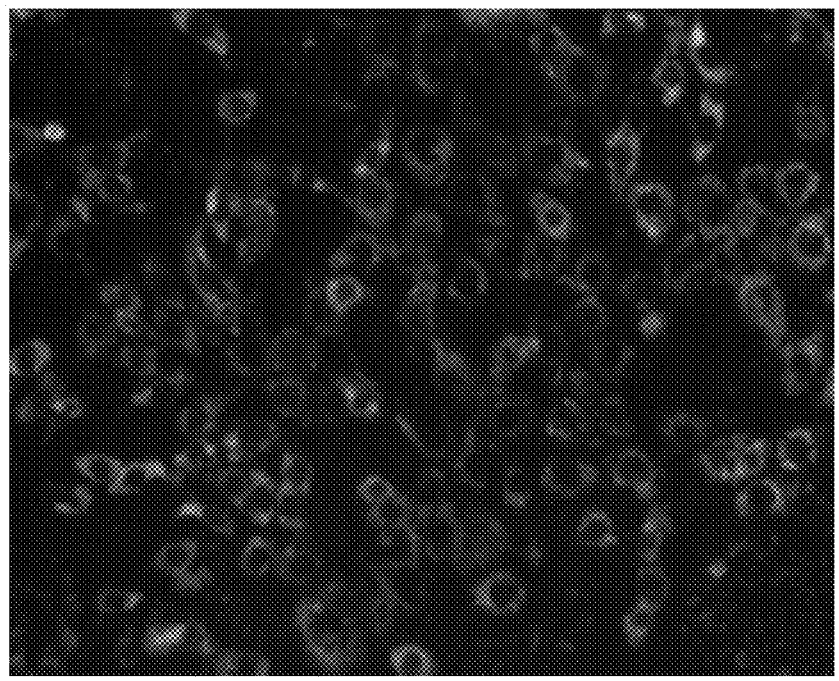
FIG. 35 shows a fluorescence image of the uptake of rhodamine from a solution of liposomes composed of 10 mol % rhodamine.
Figure 36:
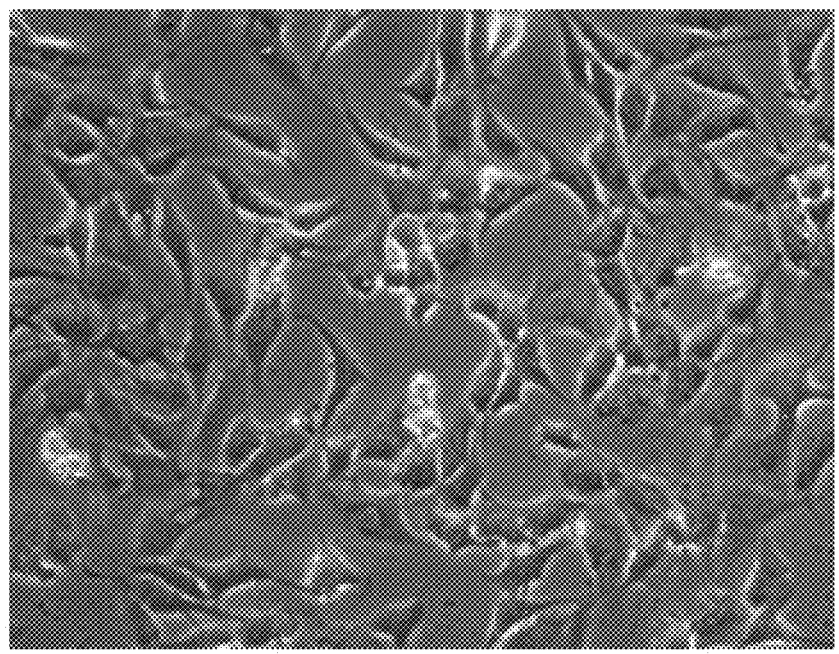
FIG. 36 shows a brightfield image of the uptake of rhodamine by the cells of FIG. 35.
Figure 37:
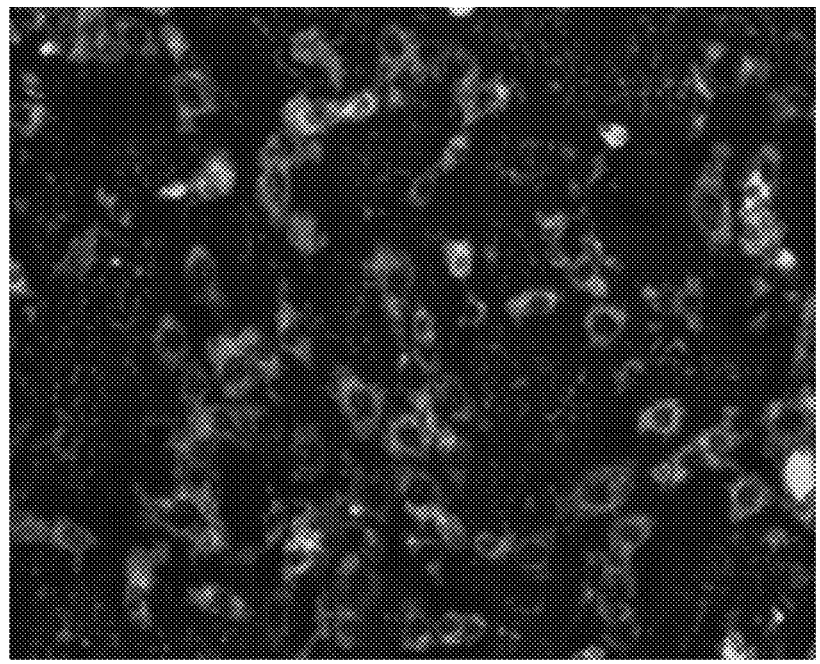
FIG. 37 shows a fluorescence image of the uptake of rhodamine from a solution of liposomes composed of 100 mol % rhodamine.
Figure 38:
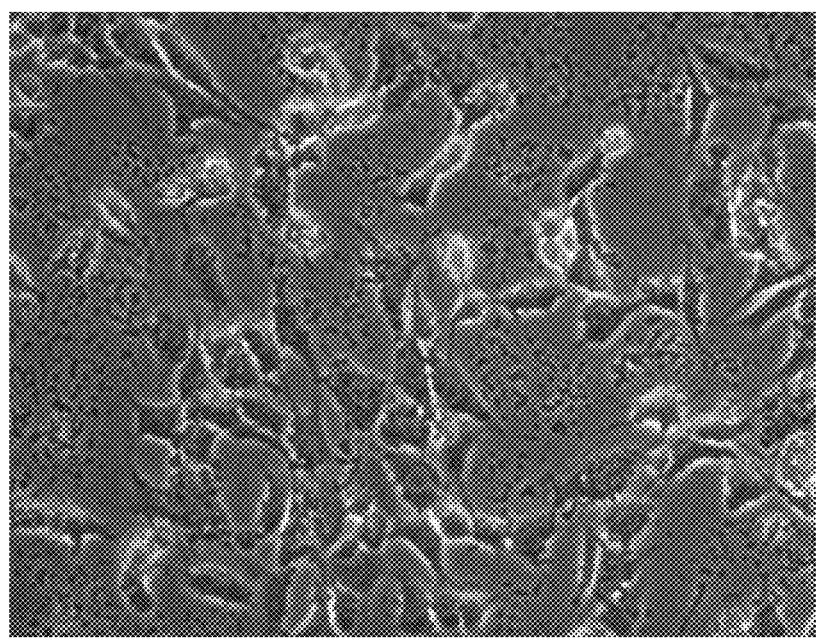
FIG. 38 shows a brightfield image of the uptake of rhodamine by the cells of FIG. 37.

Experiments are performed to determine the cell uptake of liposomes from a solution of known liposomal concentration in order to compare them with the surface-supported liposome microarrays and determine the equivalent dosages received by the cells using fluorescence based toxicity assay described in A. E. Kusi-appiah, N. Vafai, P. Cranfil, M. W. Davidson and S. Lenhert, "Lipid multilayer microarrays for in vitro liposomal drug delivery and screening," *Biomaterials* 33, 4187-91 (2012). FIG. 33 shows a fluorescence image of the uptake of the fluorophore (fluorescent molecule) rhodamine from a solution of liposomes composed of 1 mol % rhodamine. FIG. 34 shows a brightfield image of the uptake of rhodamine by the cells of FIG. 33. FIG. 35 shows a fluorescence image of the uptake of rhodamine from a solution of liposomes composed of 10 mol % rhodamine. FIG. 36 shows a brightfield image of the uptake of rhod-amine by the cells of FIG. 35. FIG. 37 shows a fluorescence image of the uptake of rhodamine from a solution of liposomes composed of 100 mol % rhodamine. FIG. 38 shows a brightfield image of the uptake of rhodamine by the cells of FIG. 37.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as nonlimiting examples and are, therefore, not to be taken as limiting the various aspects so illustrated.

While the present invention has been disclosed with references to certain embodiments, numerous modifications, alterations and changes to the described embodiments are possible without departing from the spirit and scope of the present invention, as defined in the appended claims. Accordingly, it is intended that the present invention not be limited to the described embodiments, but that it have the full scope defined by the language of the following claims, and equivalents thereof.

REFERENCES

Various techniques described above that may be used with the present invention are described in A. E. Kusi-appiah, N. Vafai, P. Cranfil, M. W. Davidson and S. Lenhert, "Lipid multilayer microarrays for in vitro liposomal drug delivery and screening," *Biomaterials* 33, 4187-91 (2012), the entire contents and disclosure of which are incorporated herein by reference.

The following references are referred to above and are incorporated herein by reference:
1. A. Dove, "High-throughput screening goes to school," *Nat. Methods* 4, 523-9 (2007).
2. J. A. DiMasi, R. W. Hansen, H. G. Grabowski, "The price of innovation: new estimates of drug development costs," *J. Health Econ.* 22, 151-85 (2003).
3. L. F. Kang, B. G. Chung, R. Langer, A. Khademhosseini, "Microfluidics for drug discovery and development: from target selection to product lifecycle management," *Drug Discov. Today* 13, 1-13 (2008).
4. F. Xu, J. H. Wu, S. Q. Wang, N. G. Durmus, U. A. Gurkan, U. Demirci, "Microengineering methods for cell-based microarrays and high-throughput drug-screening applications," *Biofabrication* 3, 034101 (2011).
5. P. S. Dittrich, A. Manz, "Lab-on-a-chip: microfluidics in drug discovery," *Nat. Rev. Drug Discov.* 5, 210-18 (2006).
6. D. B. Weibel, G. M. Whitesides, "Applications of microfluidics in chemical biology," *Curr. Opin. Chem. Biol.* 10, 584-91 (2006).
7. G. M. Whitesides, "The origins and the future of microfluidics," *Nature* 442, 368-73 (2006).
8. H. Y. Wang, N. Bao, C. Lu, "A microfluidic cell array with individually addressable culture chambers," *Biosens. Bioelectron.* 24, 613-17 (2008).
9. R. Gomez-Sjoberg, A. A. Leyrat, D. M. Pirone, C. S. Chen, S. R. Quake, "Versatile, fully automated, microfluidic cell-culture system," *Anal. Chem.* 79, 8557-63 (2007).
10. I. Meyvantsson, J. W. Warrick, S. Hayes, A. Skoien, D. J. Beebe, "Automated cell culture in high density tubeless microfluidic device arrays," *Lab Chip* 8, 717-24 (2008).

11. L. Y. Wu, D. Di Carlo, L. P. Lee, "Microfluidic self-assembly of tumor spheroids for anticancer drug discovery," *Biomed. Microdevices* 10, 197-202 (2008).
12. A. Khademhosseini, R. Langer, J. Borenstein, J. P. Vacanti, "Microscale technologies for tissue engineering and biology," *Proc. Natl. Acad. Sci. USA* 103, 2480-87 (2006).
13. M. L. Yarmush, K. R. King, "Living-cell microarrays," *Annu. Rev. Biomed. Eng.* 11, 235-57 (2009).
14. V. Starkuviene, R. Pepperkok, H. Erflef, "Transfected cell microarrays: an efficient tool for high-throughput functional analysis," *Expert Rev. Proteomics* 4, 479-89 (2007).
15. D. S. Chen, M. M. Davis, "Molecular and functional analysis using live cell microarrays," *Curr. Opin. Chem. Biol.* 10, 28-34 (2006).
16. R. L. Nicholson, M. Welch, M. Ladlow, D. R. Spring, "Small-molecule screening: advances in microarraying and cell-imaging technologies," *ACS Chem. Biol.* 2, 24-30 (2007).
17. M. Hoever, P. Zbinden, "The evolution of microarrayed compound screening," *Drug Discov. Today* 9, 358-65 (2004).
18. A. L. Hook, H. Thissen, N. H. Voelcker, "Advanced substrate fabrication for cell microarrays," *Biomacromolecules* 10, 573-79 (2009).
19. S, N. Bailey, D. M. Sabatini, B. R. Stockwell, "Microarrays of small molecules embedded in biodegradable polymers for use in mammalian cell-based screens," *Proc. Natl. Acad. Sci. USA* 101, 16144-9 (2004).
20. P. J. Hung, P. J. Lee, P. Sabounchi, R. Lin, L. P. Lee, "Continuous perfusion microfluidic cell culture array for high-throughput cell-based assays," *Biotechnol. Bioeng.* 89, 1-8 (2005).
21. S. Upadhyaya, P. R. Selvaganaphthy, "Microfluidic devices for cell based high throughput screening," *Lab Chip* 10, 341-8 (2010).
22. J. H. Wu, I. Wheeldon, Y. Q. Guo, T. L. Lu, Y. N. Du, B. Wang, J. He, Y. Hu, A. Khademhosseini, "A sandwiched microarray platform for benchtop cell-based high throughput screening," *Biomaterials* 32, 841-48 (2011).
23. E. Koren, V. P. Torchilin, "Drug carriers for vascular drug delivery," *IUBMB Life* 63, 586-95 (2011).
24. G. Gregoriadis, "Engineering liposomes for drug delivery: progress and problems," *Trends Biotechnol.* 13, 527-37 (1995).
25. C. H. Kwon, I. Wheeldon, N. N. Kachouie, S. H. Lee, H. Bae, S. Sant, J. Fukuda, J. Kang, W. Jeong, A. Khademhosseini, "Drug-eluting microarrays for cell-based screening of chemical-induced apoptosis," *Anal. Chem.* 83(11), 4118-25 (2011).
26. Y. Malam, M. Loizidou, A. M. Seifalian, "Liposomes and nanoparticles: nanosized vehicles for drug delivery in cancer," *Trends Pharmacol. Sci.* 30, 592-99 (2009).
27. C. J. H. Porter, N. L. Trevaskis, W. N. Charman, "Lipids and lipid-based formulations: optimizing the oral delivery of lipophilic drugs," *Nat. Rev. Drug Discov.* 6, 231-48 (2007).
28. V. P. Torchilin, "Micellar nanocarriers: pharmaceutical perspectives," *Pharm. Res.* 24, 1-16 (2007).
29. S. Lenhert, F. Brinkmann, T. Laue, S. Walheim, C. Vannahme, S. Klinkhammer, M. Xu, S. Sekula, T. Mappes, T. Schimmel, H. Fuchs, "Lipid multilayer gratings," *Nat. Nanotechnol.* 5(4), 275-79 (2010).
30. S. Lenhert, H. Fuchs, "Lipid dip-pen nanolithography for functional biomimetic membrane systems," *Nanotechnology* 1, 513-16 (2008).
31. S. Lenhert, P. Sun, Y. H. Wang, H. Fuchs, C. A. Mirkin, "Massively parallel dip-pen nanolithography of heterogeneous supported phospholipid multilayer patterns," *Small* 3, 71-75 (2007).
32. S. Sekula, J. Fuchs, S. Weg-Remers, P. Nagel, S. Schuppler, J. Fragala, N. Theilacker, M. Franzreb, C. Wingren, P. Ellmark, C. A. K. Borrebaeck, C. A. Mirkin, H. Fuchs, S. Lenhert, "Multiplexed lipid dip-pen nanolithography on subcellular scales for the templating of functional proteins and cell culture," *Small* 4, 1785-93 (2008).
33. K. Salaita, Y. H. Wang, J. Fragala, R. A. Vega, C. Liu, C. A. Mirkin, "Massively parallel dip-pen nanolithography with 55000-pen two-dimensional arrays," *Angew. Chem. Int. Ed.* 45, 7220-23 (2006).
34. M. Shimazawa, Y. Inokuchi, Y. Ito, H. Murata, M. Aihara, M. Miura M, A. Makoto Araie, H. Hideaki, "Involvement of ER stress in retinal cell death," *Mol. Vis.* 13, 578-87 (2007).
35. C. Riccardi, I. Nicoletti, "Analysis of apoptosis by propidium iodide staining and flow cytometry," *Nat. Protoc.* 1(3), 1458-61 (2006).
36. T. DeLigio, A. Velkova, D. A. R. Zorio, A. Monteiro, "Can BRCA1 predict response to taxane-based cancer therapy?" *Anticancer Agents Med. Chem.* 9, 543-49 (2009).
37. D. J. Kenan, E. B. Walsh, S. R. Meyers, G. A. O'Toole, E. G. Carruthers, W. K. Lee, S. Zauscher, C. A. Prata, M. W. Grinstaff, "Peptide-PEG amphiphiles as cytophobic coatings for mammalian and bacterial cells," *Chem. Biol.* 13, 695-700 (2006).
38. O. A. Nafday, S. Lenhert, "High-throughput optical quality control of lipid multilayers fabricated by dip-pen nanolithography," *Nanotechnology* 22, 225301 (2011).
39. Y. Wang, L. R. Giam, M. Park, S. Lenhert, H. Fuchs, C. A. Mirkin, "A self-correcting inking strategy for cantilever arrays addressed by an inkjet printer and used for dip-pen nanolithography," *Small* 4, 1666-70 (2008).
40. O. A. Nafday, T. W. Lowry, S. Lenhert, "Multifunctional lipid multilayer stamping," *Small* 8(7), 1021-28 (2012).
41. S. Sekula, J. Fuchs, S. Weg-Remers, P. Nagel, S. Schuppler, J. Fragala, N. Theilacker, M. Franzreb, C. Wingren, P. Ellmark, C. A. K. Borrebaeck, C. A. Mirkin, H. Fuchs, S. Lenhert, "Multiplexed lipid dip-pen nanolithography on subcellular scales for templating of functional proteins and cell culture," *Small* 4, 1785-93 (2008).
42. S. Lenhert, P. Sun, Y. H. Wang, H. Fuchs, C. A. Mirkin, "Massively parallel dip-pen nanolithography of heterogeneous supported phospholipid multilayer patterns," *Small* 3, 71-75 (2007).
43. U.S. patent application Ser. No. 13/417,588 to Lenhert et al., entitled "Method and apparatus for lipid multilayer patterning," filed Mar. 12, 2012.
44. R. L. Nicholson, M. Welch, M. Ladlow, D. R. Spring, "Small-molecule screening: Advances in microarraying and cell-imaging technologies," *ACS Chem. Biol.* 2, 24-30 (2007).

What is claimed is:
1. A device comprising:
a substrate,
one or more lipid multilayer arrays on a surface of the substrate,
wherein the one or more lipid multilayer arrays are directly printed onto the surface of the substrate by dip-pen nanolithography, wherein each lipid multilayer array of the one or more lipid multilayer arrays comprises one or more lipid multilayer structures, wherein each lipid multilayer structure of the one or more lipid multilayer structures is a surface-supported lipid multilayer structure, wherein each lipid multilayer structure of the one or more lipid multilayer structures encapsulates an encapsulated material, wherein when a cell is in contact with one or more lipid multilayer structures of the one or more lipid multilayer structures, the one or more contacted lipid multilayer structures deliver the encapsulated material to the cell, and wherein each of the one or more lipid multilayer structures is a microstructure.

2. The device of claim 1, wherein each lipid multilayer structure is a nanostructure.

3. The device of claim 1, wherein the device comprises:
a first lipid multilayer array of first lipid multilayer structures, and
a second lipid multilayer array of second lipid multilayer structures,
wherein a first encapsulated material is encapsulated in the first lipid multilayer structures,
wherein a second encapsulated material is encapsulated in the second lipid multilayer structures, and
wherein the first encapsulated material is different from the second encapsulated material.

4. The device of claim 1, wherein the device comprises a plurality of cells in contact with the one or more lipid multilayer arrays.

5. The device of claim 1, wherein at least one of the one or more lipid multilayer structures encapsulates a drug.

6. The device of claim 1, wherein one or more first lipid multilayer structures of the one or more lipid multilayer structures encapsulate a first dosage of a drug and wherein one or more second lipid multilayer structures of the one or more lipid multilayer structures encapsulate a second dosage of the drug that is different from the first dosage of the drug.

7. The device of claim 1, wherein the one or more lipid multilayer structures comprise 1,2-dioleoyl-3-trimethylammoniumpropane (chloride salt) (DOTAP).

8. The device of claim 1, wherein each encapsulated material is fluorescently tagged.

9. The device of claim 1, wherein the one or more lipid multilayer arrays are organized in a regular pattern on the substrate.

10. A device comprising:
a substrate,
one or more lipid multilayer arrays on a surface of the substrate,
wherein the one or more lipid multilayer arrays are directly printed onto the surface of the substrate by lipid ink in contact with the substrate being pulled from one or more recesses of a stamp,
wherein each lipid multilayer array of the one or more lipid multilayer arrays comprises one or more lipid multilayer structures,
wherein each lipid multilayer structure of the one or more lipid multilayer structures is a surface-supported lipid multilayer structure,
wherein each lipid multilayer structure of the one or more lipid multilayer structures encapsulates an encapsulated material,
wherein when a cell is in contact with one or more lipid multilayer structures of the one or more lipid multilayer structures, the one or more contacted lipid multilayer structures deliver the encapsulated material to the cell, and wherein each of the one or more lipid multilayer structures is a microstructure.

11. The device of claim 10, wherein each lipid multilayer structure is a nanostructure.

12. The device of claim 10, wherein the device comprises:
a first lipid multilayer array of first lipid multilayer structures, and
a second lipid multilayer array of second lipid multilayer structures,
wherein a first encapsulated material is encapsulated in the first lipid multilayer structures,
wherein a second encapsulated material is encapsulated in the second lipid multilayer structures, and
wherein the first encapsulated material is different from the second encapsulated material.

13. The device of claim 10, wherein the device comprises a plurality of cells in contact with the one or more lipid multilayer arrays.

14. The device of claim 10, wherein at least one of the one or more lipid multilayer structures encapsulates a drug.

15. The device of claim 10, wherein one or more first lipid multilayer structures of the one or more lipid multilayer structures encapsulate a first dosage of a drug and wherein one or more second lipid multilayer structures of the one or more lipid multilayer structures encapsulate a second dosage of the drug that is different from the first dosage of the drug.

16. The device of claim 10, wherein the one or more lipid multilayer structures comprise 1,2-dioleoyl-3-trimethylammoniumpropane (chloride salt) (DOTAP).

17. The device of claim 10, wherein each encapsulated material is fluorescently tagged.

18. The device of claim 10, wherein the one or more lipid multilayer arrays are organized in a regular pattern on the substrate.

19. The device of claim 10, wherein the one or more lipid multilayer structures have a thickness of 10 to 100 nanometers.

20. The device of claim 10, wherein the one or more lipid multilayer structures have a thickness of more than 100 nanometers.

21. The device of claim 10, wherein the one or more lipid multilayer structures have a thickness of 10 to 200 nanometers.

22. A device comprising:
a substrate,
one or more lipid multilayer arrays directly printed onto a surface of the substrate,
wherein each lipid multilayer array of the one or more lipid multilayer arrays comprises one or more lipid multilayer structures,
wherein each lipid multilayer structure of the one or more lipid multilayer structures is a surface-supported lipid multilayer structure,
wherein each lipid multilayer structure of the one or more lipid multilayer structures encapsulates an encapsulated material,
wherein when a cell is in contact with one or more lipid multilayer structures of the one or more lipid multilayer structures, the one or more contacted lipid multilayer structures deliver the encapsulated material to the cell, and wherein each of the one or more lipid multilayer structures is a microstructure.

* * * * *